(12) United States Patent
Keckler et al.

(10) Patent No.: US 8,057,661 B2
(45) Date of Patent: *Nov. 15, 2011

(54) PROCESS FOR REMOVAL OF SULFUR FROM COMPONENTS FOR BLENDING OF TRANSPORTATION FUELS

(75) Inventors: Kenneth Paul Keckler, Naperville, IL (US); Avelino Corma, Valencia (ES); Thomas Knox, Crowthorne (GB); Paul Greenough, Beaconsfield (GB); Michael Graham Hodges, Wonersh (GB)

(73) Assignee: BP Corporation North America Inc., Houston, TX (US)

( * ) Notice: Subject to any disclaimer, the term of this patent is extended or adjusted under 35 U.S.C. 154(b) by 117 days.

This patent is subject to a terminal disclaimer.

(21) Appl. No.: 11/722,217

(22) PCT Filed: Dec. 22, 2005

(86) PCT No.: PCT/US2005/047173
§ 371 (c)(1),
(2), (4) Date: Apr. 25, 2008

(87) PCT Pub. No.: WO2006/073963
PCT Pub. Date: Jul. 13, 2006

(65) Prior Publication Data
US 2008/0302704 A1 Dec. 11, 2008

(51) Int. Cl.
*C10G 25/00* (2006.01)
*C10G 35/04* (2006.01)
(52) U.S. Cl. ........ 208/91; 208/254 R; 208/302; 208/134
(58) Field of Classification Search .................... 208/91, 208/134, 254 R, 302
See application file for complete search history.

(56) References Cited

U.S. PATENT DOCUMENTS

| | | | |
|---|---|---|---|
| 4,550,090 A | 10/1985 | Degnan et al. | 502/25 |
| 4,567,315 A | 1/1986 | Owaysi et al. | 585/827 |
| 5,220,099 A * | 6/1993 | Schreiner et al. | 585/820 |
| 5,492,874 A | 2/1996 | Corma Canos et al. | 502/64 |
| 5,863,419 A | 1/1999 | Huff, Jr. et al. | 208/237 |
| 6,019,887 A * | 2/2000 | Ramirez de Agudelo et al. | 208/254 R |
| 6,136,181 A | 10/2000 | Ziemer | 208/144 |
| 6,329,562 B1 | 12/2001 | Wohrle et al. | 585/820 |
| 6,444,865 B1 | 9/2002 | Barre et al. | 585/266 |
| 6,733,660 B2 | 5/2004 | Pradhan et al. | |
| 7,087,156 B2 * | 8/2006 | Lesemann et al. | 208/211 |
| 2003/0034276 A1 * | 2/2003 | Pradhan et al. | 208/208 R |
| 2004/0178122 A1 | 9/2004 | Karas et al. | |

FOREIGN PATENT DOCUMENTS

EP 1002852 5/2000
WO WO 2005/019391 3/2005

OTHER PUBLICATIONS

Hernández-Maldonado, A and Yang, R., Denitrogenation of Transportation Fuels by Zeolites at Ambient Temperature and Pressure, 3 pages, Oct. 27, 2003.
The Merck Index, 9th Edition, 1976, p. 1033, paragraph 7752 (Pyridline).
The Merck Index, 9th Edition, 1976, p. 1246, paragraph 9379 (Trimethylamine).

* cited by examiner

Primary Examiner — Walter Griffin
Assistant Examiner — Renee Robinson

(57) ABSTRACT

A process is disclosed for removing highly deleterious non-basic nitrogen compounds upstream from an acid catalyzed thiophene alkylation process using adsorbents capable of adsorbing the non-basic nitrogen compounds.

7 Claims, 16 Drawing Sheets

Depicts results of the same runs except thiophene conversion is plotted as a function of nitrogen adsorbed on to the solid phosphoric acid catalyst.

PROCESS FOR REMOVAL OF SULFUR FROM COMPONENTS FOR BLENDING OF TRANSPORTATION FUELS

CROSS-REFERENCE TO RELATED APPLICATIONS

This application is the U.S. national phase of International Application No. PCT/US2005/047173, filed Dec. 22, 2005, which designated the U.S. and which claims priority benefit of U.S. patent application Ser. No. 11/026,204, filed on Dec. 30, 2004, the disclosure of which is incorporated herein by reference.

TECHNICAL FIELD

The present invention relates to fuels for transportation which are liquid at ambient conditions and typically derived from natural petroleum. Broadly, it relates to integrated, processes for producing products of reduced sulfur content from a feedstock wherein the feedstock is comprised of limited amounts of sulfur-containing organic compounds as unwanted impurities. More particularly, the invention relates to integrated, processes which include treatment of a refinery stream with a solid adsorbent to remove non-basic nitrogen-containing compounds, chemical conversion of one or more of the sulfur-containing impurities to higher boiling products by alkylation using an acidic catalyst contacting stage at elevated temperatures. The alkylated sulfur compounds can then be concentrated by distillation and further treated by hydrogenation for removal of the sulfur. The products can be used directly as transportation fuels and/or blending components to provide fuels which are more friendly to the environment.

BACKGROUND OF THE INVENTION

It is well known that internal combustion engines have revolutionized transportation following their invention during the last decades of the 19th century. While others, including Benz and Gottleib Wilhelm Daimler, invented and developed engines using electric ignition of fuel such as gasoline, Rudolf C. K. Diesel invented and built the engine named for him which employs compression for auto-ignition of the fuel in order to utilize low-cost organic fuels. Equal, if not more important, development of improved spark-ignition engines for use in transportation has preceded hand-in-hand with improvements in gasoline fuel compositions. Modern high performance gasoline engines demand ever more advanced specification of fuel compositions, but cost remains an important consideration.

At the present time most fuels for transportation are derived from natural petroleum. Indeed, petroleum as yet is the world's main source of hydrocarbons used as fuel and petrochemical feedstock. While compositions of natural petroleum or crude oils are significantly varied, all crudes contain sulfur compounds and most contain nitrogen compounds which may also contain oxygen, but oxygen content of most crudes is low. Generally, sulfur concentration in crude is less than about 8 percent, with most crudes having sulfur concentrations in the range from about 0.5 to about 1.5 percent. Nitrogen concentration is usually less than 0.2 percent, but it may be as high as 1.6 percent.

Crude oil seldom is used in the form produced at the well, but is converted in oil refineries into a wide range of fuels and petrochemical feedstocks. Typically fuels for transportation are produced by processing and blending of distilled fractions from the crude to meet the particular end use specifications. Because most of the crudes available today in large quantity are high in sulfur, the distilled fractions must be desulfurized to yield products which meet performance specifications and/or environmental standards. Sulfur containing organic compounds in fuels continue to be a major source of environmental pollution. During combustion they are converted to sulfur oxides which, in turn, give rise to sulfur oxyacids and, also, contribute to particulate emissions.

In the face of ever-tightening sulfur specifications in transportation fuels, sulfur removal from petroleum feedstocks and products will become increasingly important in years to come. While legislation on sulfur in diesel fuel in Europe, Japan and the U.S. has recently lowered the specification to 0.05 percent by weight (max.), indications are that future specifications may go far below the current 0.05 percent by weight level. Legislation on sulfur in gasoline in the U.S. now limits each refinery to an average of 30 parts per million. In and after 2006 the average specification will be replaced by a cap of 80 parts per million maxim.

The fluidized catalytic cracking process is one of the major refining processes which is currently employed in the conversion of petroleum to desirable fuels such as gasoline and diesel fuel. In this process, a high molecular weight hydrocarbon feedstock is converted to lower molecular weight products through contact with hot, finely-divided, solid catalyst particles in a fluidized or dispersed state. Suitable hydrocarbon feedstocks typically boil within the range of 205° C. to about 650° C., and they are usually contacted with the catalyst at temperatures in the range 450° C. to about 650° C. Suitable feedstocks include various mineral oil fractions such as light gas oils, heavy gas oils, wide-cut gas oils, vacuum gas oils, kerosenes, decanted oils, residual fractions, reduced crude oils and cycle oils which are derived from any of these as well as fractions derived from shale oils, tar sands processing, and coal liquefaction. Products from a fluidized catalytic cracking process are typically based on boiling point and include light naphtha (boiling between about 10° C. and about 221° C.), heavy naphtha (boiling between about 10° C. and about 249° C.), kerosene (boiling between about 180° C. and about 300° C.), light cycle oil (boiling between about 221° C. and about 345° C.), and heavy cycle oil (boiling at temperatures higher than about 345° C.).

Not only does the fluidized catalytic cracking process provide a significant part of the gasoline pool in the United States, it also provides a large proportion of the sulfur that appears in this pool. The sulfur in the liquid products from this process is in the form of organic sulfur compounds and is an undesirable impurity which is converted to sulfur oxides when these products are utilized as a fuel. These sulfur oxides are objectionable air pollutants. In addition, they can deactivate many of the catalysts that have been developed for the catalytic converters which are used on automobiles to catalyze the conversion of harmful engine exhaust emissions to gases which are less objectionable. Accordingly, it is desirable to reduce the sulfur content of catalytic cracking products to the lowest possible levels.

The sulfur-containing impurities of straight run gasolines, which are prepared by simple distillation of crude oil, are usually very different from those in cracked gasolines. The former contain mostly mercaptans and sulfides, whereas the latter are rich in thiophene, benzothiophene and derivatives of thiophene and benzothiophene.

Low sulfur products are conventionally obtained from the catalytic cracking process by hydrotreating either the feedstock to the process or the products from the process. Hydrotreating involves treatment of products of the cracking process with hydrogen in the presence of a catalyst and results in the conversion of the sulfur in the sulfur-containing impurities to hydrogen sulfide, which can be separated and converted to elemental sulfur. Unfortunately, this type of processing is typically quite expensive because it requires a source of hydrogen, high pressure process equipment, expensive hydrotreating catalysts, and a sulfur recovery plant for conversion of the resulting hydrogen sulfide to elemental sulfur. In addition, the hydrotreating process can result in an undesired destruction of olefins in the feedstock by converting them to saturated hydrocarbons through hydrogenation. This destruction of olefins by hydrogenation is usually undesirable because it results in the consumption of expensive hydrogen, and also because the olefins are valuable as high octane components of gasoline. As an example, naphtha of a gasoline boiling range from a catalytic cracking process has a relatively high octane number as a result of a large olefin content. Hydrotreating such a material causes a reduction in the olefin content in addition to the desired desulfurization, and the octane number of the hydrotreated product decreases as the degree of desulfurization increases.

Conventional hydrodesulfurization catalysts can be used to remove a major portion of the sulfur from petroleum distillates for the blending of refinery transportation fuels, but they are not efficient for removing sulfur from compounds where the sulfur atom is sterically hindered as in multi-ring aromatic sulfur compounds. This is especially true where the sulfur heteroatom is doubly hindered (e.g., 4,6-dimethyldibenzothiophene). Using conventional hydrodesulfurization catalysts at high temperatures would cause yield loss, faster catalyst coking, and product quality deterioration (e.g., color). Using high pressure requires a large capital outlay. Accordingly, there is a need for an inexpensive process for the effective removal of sulfur-containing impurities from distillate hydrocarbon liquids. There is also a need for such a process which can be used to remove sulfur-containing impurities from distillate hydrocarbon liquids, such as products from a fluidized catalytic cracking process, which are highly olefinic and contain both thiophenic and benzothiophenic compounds as unwanted impurities.

In order to meet stricter specifications in the future, such hindered sulfur compounds will also have to be removed from distillate feedstocks and products. There is a pressing need for economical removal of sulfur from refinery fuels for transportation, especially from components for gasoline.

The art is replete with processes said to remove sulfur from distillate feedstocks and products.

U.S. Pat. No. 2,448,211, in the name of Philip D. Caesar, et al. states that thiophene and its derivatives can be alkylated by reaction with olefinic hydrocarbons at a temperature between about 140° and about 400° C. in the presence of a catalyst such as an activated natural clay or a synthetic adsorbent composite of silica and at least one amphoteric metal oxide. Suitable activated natural clay catalysts include clay catalysts on which zinc chloride or phosphoric acid have been precipitated. Suitable silica-amphoteric metal oxide catalysts include combinations of silica with materials such as alumina, zirconia, ceria, and thoria. U.S. Pat. No. 2,469,823, in the name of Rowland C. Hansford and Philip D. Caesar teaches that boron trifluoride can be used to catalyze the alkylation of thiophene and alkyl thiophenes with alkylating agents such as olefinic hydrocarbons, alkyl halides, alcohols, and mercaptans. In addition, U.S. Pat. No. 2,921,081, in the name of (Zimmerschied et al.) discloses that acidic solid catalysts can be prepared by combining a zirconium compound selected from the group consisting of zirconium dioxide and the halides of zirconium with an acid selected from the group consisting of ortho-phosphoric acid, pyrophosphoric acid, and triphosphoric acid. The Zimmerschied et al. reference also teaches that thiophene can be alkylated with propylene at a temperature of 227° C. in the presence of such a catalyst.

U.S. Pat. No. 2,563,087 in the name of Jerome A. Vesely states that thiophene can be removed from aromatic hydrocarbons by selective alkylation of the thiophene and separation of the resulting thiophene alkylate by distillation. The selective alkylation is carried out by mixing the thiophene-contaminated aromatic hydrocarbon with an alkylating agent and contacting the mixture with an alkylation catalyst at a carefully controlled temperature in the range from about −20° C. to about 85° C. It is disclosed that suitable alkylating agents include olefins, mercaptans, mineral acid esters, and alkoxy compounds such as aliphatic alcohols, ethers and esters of carboxylic acids. It is also disclosed that suitable alkylation catalysts include the following: (1) the Friedel-Crafts metal halides, which are preferably used in anhydrous form; (2) a phosphoric acid, preferably pyrophosphoric acid, or a mixture of such a material with sulfuric acid in which the volume ratio of sulfuric to phosphoric acid is less than about 4:1; and (3) a mixture of a phosphoric acid, such as ortho-phosphoric acid or pyrophosphoric acid, with a siliceous adsorbent, such as kieselguhr or a siliceous clay, which has been calcined to a temperature of from about 400° to about 500° C. to form a silico-phosphoric acid combination which is commonly referred to as a solid phosphoric acid catalyst.

U.S. Pat. No. 4,775,462 in the name of Tamotsu Imai and Jeffery C. Bricker describes a method a non-oxidative method of sweetening a sour hydrocarbon fraction whereby mercaptans are converted to thioethers which are said to be acceptable in fuels. The method involves contacting a mercaptan-containing hydrocarbon fraction with a catalyst consisting of an acidic inorganic oxide, a polymeric sulfonic acid resin, an intercalate compound, a solid acid catalyst, a boron halide dispersed on alumina, or an aluminum halide dispersed on alumina, in the presence of an unsaturated hydrocarbon equal to the molar amount of mercaptans, typically from about 0.01 weight percent to bout 20 weight percent. While the product is said to be substantially free of mercaptans, the level of elemental sulfur his not been reduced by this process.

U.S. Pat. No. 5,171,916 in the name of Quany N. Le and Michael S. Sarli describes a process for upgrading a light cycle oil by: (A) alkylating the heteroatom containing aromatics of the cycle oil with an aliphatic hydrocarbon having 14 to 24 carbon atoms and at least one olefinic double bond through the use of a crystalline metallosilicate catalyst; and (B) separating the high boiling alkylation product in the lubricant boiling range from the unconverted light cycle oil by fractional distillation. It also states that the unconverted light cycle oil has a reduced sulfur and nitrogen content, and the high boiling alkylation product is useful as a synthetic alkylated aromatic lubricant base stock.

U.S. Pat. No. 5,599,441 in the name of Nick A. Collins and Jeffrey C. Trewella describes a process for removing thiophenic sulfur compounds from a cracked naphtha by: (A) contacting the naphtha with an acid catalyst to alkylate the thiophenic compounds using the olefins present in the naphtha as an alkylating agent; (B) removing an effluent stream from the alkylation zone; and (C) separating the alkylated thiophenic compounds from the alkylation zone effluent stream by fractional distillation. It also states that additional olefins can be added to the cracked naphtha to provide additional alkylating agent for the process.

More recently, U.S. Pat. No. 6,024,865 in the name of Bruce D. Alexander, George A. Huff, Vivek R. Pradhan, William J. Reagan and Roger H. Cayton disclosed a product of reduced sulfur content which is produced from a feedstock which is comprised of a mixture of hydrocarbons and includes sulfur-containing aromatic compounds as unwanted impurities. The process involves separating the feedstock by fractional distillation into a lower boiling fraction which contains the more volatile sulfur-containing aromatic impurities and at least one higher boiling fraction which contains the less volatile sulfur-containing aromatic impurities. Each fraction is then separately subjected to reaction conditions which are effective to convert at least a portion of its content of sulfur-containing aromatic impurities to higher boiling sulfur-containing products by alkylation with an alkylating agent in the presence of an acidic catalyst. The higher boiling sulfur-containing products are removed by fractional distillation. It is also stated that alkylation can be achieved in stages with the proviso that the conditions of alkylation are less severe in the initial alkylation stage than in a secondary stage, e.g., through the use of a lower temperature in the first stage as opposed to a higher temperature in a secondary stage.

U.S. Pat. No. 6,059,962 in the name of Bruce D. Alexander, George A. Huff, Vivek R. Pradhan, William J. Reagan and Roger H. Clayton disclosed a product of reduced sulfur content is produced in a multiple stage process from a feedstock which is comprised of a mixture of hydrocarbons and includes sulfur-containing aromatic compounds as unwanted impurities. The first stage involves: (1) subjecting the feedstock to alkylation conditions which are effective to convert a portion of the impurities to higher boiling sulfur-containing products, and (2) separating the resulting products by fractional distillation into a lower boiling fraction and a higher boiling fraction. The lower boiling fraction is comprised of hydrocarbons and is of reduced sulfur content relative to the feedstock. The higher boiling fraction is comprised of hydrocarbons and contains unconverted sulfur-containing aromatic impurities and also the higher boiling sulfur-containing products. Each subsequent stage involves: (1) subjecting the higher boiling fraction from the preceding stage to alkylation conditions which are effective to convert at least a portion of its content of sulfur-containing aromatic compounds to higher boiling sulfur-containing products, and (2) separating the resulting products by fractional distillation into a lower boiling hydrocarbon fraction and a higher boiling fraction which contains higher boiling sulfur-containing alkylation products. The total hydrocarbon product of reduced sulfur content from the process is comprised of the lower boiling fractions from various stages. Again it is stated that alkylation can be achieved in stages with the proviso that the conditions of alkylation are less severe in the initial alkylation stage than in a secondary stage, e.g., through the use of a lower temperature in the first stage a opposed to a higher temperature in a secondary stage.

The need for removing certain nitrogen compounds upstream of various processes has also been recognized in the art.

For instance, U.S. Pat. No. 6,602,405B2 (Pradhan et al.) discloses process for producing products having a reduced sulfur content wherein basic nitrogen containing impurities are removed from the feed stock prior to passing the feedstock to an olefin-modification reaction zone using a solid phosphoric acid catalyst or an acidic polymeric resin catalyst.

U.S. Pat. No. 6,599,417B2 (Pradhan et al.) similarly teaches the removal of basic nitrogen containing impurities from a feedstock prior to passing the feedstock to an olefin modification reaction zone.

U.S. Pat. No. 6,736,660B2 (Pradhan et al.) also teaches the removal of nitrogen-containing organic compounds upstream of an acidic catalyst process.

While the prior art is cognizant of the need to remove nitrogen-containing molecules upstream of an acid catalyst based process the prior art has not recognized that the impact of non-basic nitrogen-containing organic compounds is even more severe as a catalyst poison versus basic or neutral nitrogen compounds.

Typical methods disclosed in art for removing nitrogen-containing molecules such as acid wash steps or acidic guard bed techniques will not work to remove these highly deleterious non-basic nitrogen compounds.

There is, therefore, a present need for processes to prepare products of reduced sulfur content from a feedstock wherein the feedstock is comprised of limited amounts of sulfur-containing and non-basic nitrogen-containing organic compounds where the deleterious non-basic nitrogen compounds can be readily removed before they can act as a catalyst poison.

This invention is directed to overcoming the problems set forth above in order to provide components for refinery blending of transportation fuels friendly to the environment.

SUMMARY OF THE INVENTION

Economical processes are disclosed for the production of components for refinery blending of transportation fuels by integrated, multistage processes which include treatment of a light refinery stream to remove non-basic nitrogen containing compounds, chemical conversion of one or more of the sulfur-containing impurities to higher boiling products through alkylation by olefins, and beneficially removing the higher boiling products by fractional distillation. This invention contemplates the treatment of various type hydrocarbon materials, especially hydrocarbon oils of petroleum origin which contain sulfur. In general, the sulfur contents of the oils are in excess of 1 percent, and range up to about 2 or 3 percent. Processes of the invention are particularly suitable for treatment of a refinery feedstream comprised of gasoline, kerosene, light naphtha, heavy naphtha, and light cycle oil, and preferably a naphtha from catalytic and/or thermal cracking processes.

In one aspect, this invention provides a process for the production of products which are liquid at ambient conditions and contain organic sulfur compounds of higher molecular weight than corresponding sulfur-containing compounds in the feedstock, which process comprises; (a) providing a feedstock comprising a mixture of hydrocarbons which includes olefins, and sulfur-containing organic compounds and non-basic nitrogen-containing organic compounds, the feedstock being a hydrocarbon-containing material boiling between about 60° C. and about 425° C. and having a sulfur content up to about 4,000 or 5,000 parts per million and a nitrogen content up to about 200 parts per million including a non-basic nitrogen compound content of up to 200 parts per million, (b) passing the feedstock through a bed of solid adsorbent comprising alkaline or alkaline earth faujasite type zeolite, or partially exchanged alkaline or alkaline earth faujasite zeolites with $H^+$ or transition metals of Groups IB, IIB, IVB, VIII, crystalline magnesium silicates and alkaline exchanged crystalline magnesium silicates or mixtures of all of the above under conditions suitable for adsorption within the bed, to effect selective adsorption and/or complexing of at least a portion of the contained non-basic nitrogen-containing organic compounds with the adsorbent, and thereby obtain effluent from the bed which contains less of nitrogen-containing organic compounds than the feedstock, (c) in a contacting stage at elevated temperatures, contacting the effluent with an acidic catalyst under conditions which are effective to convert a portion of the impurities e.g. thiophenes, to a sulfur-containing material of higher molecular weight through alkylation by the olefins, thereby forming a product stream.

Suitable feedstocks include products of refinery cracking processes which consists essentially of material boiling between about 60° C. and about 425° C. Preferably such refinery stream consisting essentially of material boiling between about 60° C. and about 400° C., and more preferably boiling between about 90° C. and about 375° C. Where the selected feedstock is a naphtha from a refinery cracking process, the feedstock consists essentially of material boiling between about 20° C. and about 250° C. Preferably the feedstock is a naphtha stream consisting essentially of material boiling between about 40° C. and about 225° C., and more preferably boiling between about 60° C. and about 200° C.

Beneficially for processes of the invention the feedstock is comprised of a naphtha produced by a catalytic cracking process. Preferably, the olefin content of the feedstock is at least equal on a molar basis to that of the sulfur-containing organic compounds.

Advantageously a solid phosphoric acid catalyst is used as the acidic catalyst in the thiophene alkylation contacting stage.

The elevated temperatures used in the thiophene alkylation contacting stage are in a range from about 90° C. to about 250° C. preferably at temperatures in a range from about 100° C. to about 235° C., and more preferably at temperatures in a range from about 140° C. to about 220° C.

This invention is particularly useful in reducing sulfur-containing organic compounds in the feedstock which include compounds in which the sulfur atom is sterically hindered, as for example in multi-ring aromatic sulfur compounds. Typically, the sulfur-containing organic compounds include at least sulfides, heteroaromatic sulfides, and/or compounds selected from the group consisting of substituted benzothiophenes and dibenzothiophenes.

For a more complete understanding of the present invention, reference should now be made to the embodiments illustrated in greater detail in the accompanying drawing and described below by way of examples of the invention.

GENERAL DESCRIPTION

Figure 1:
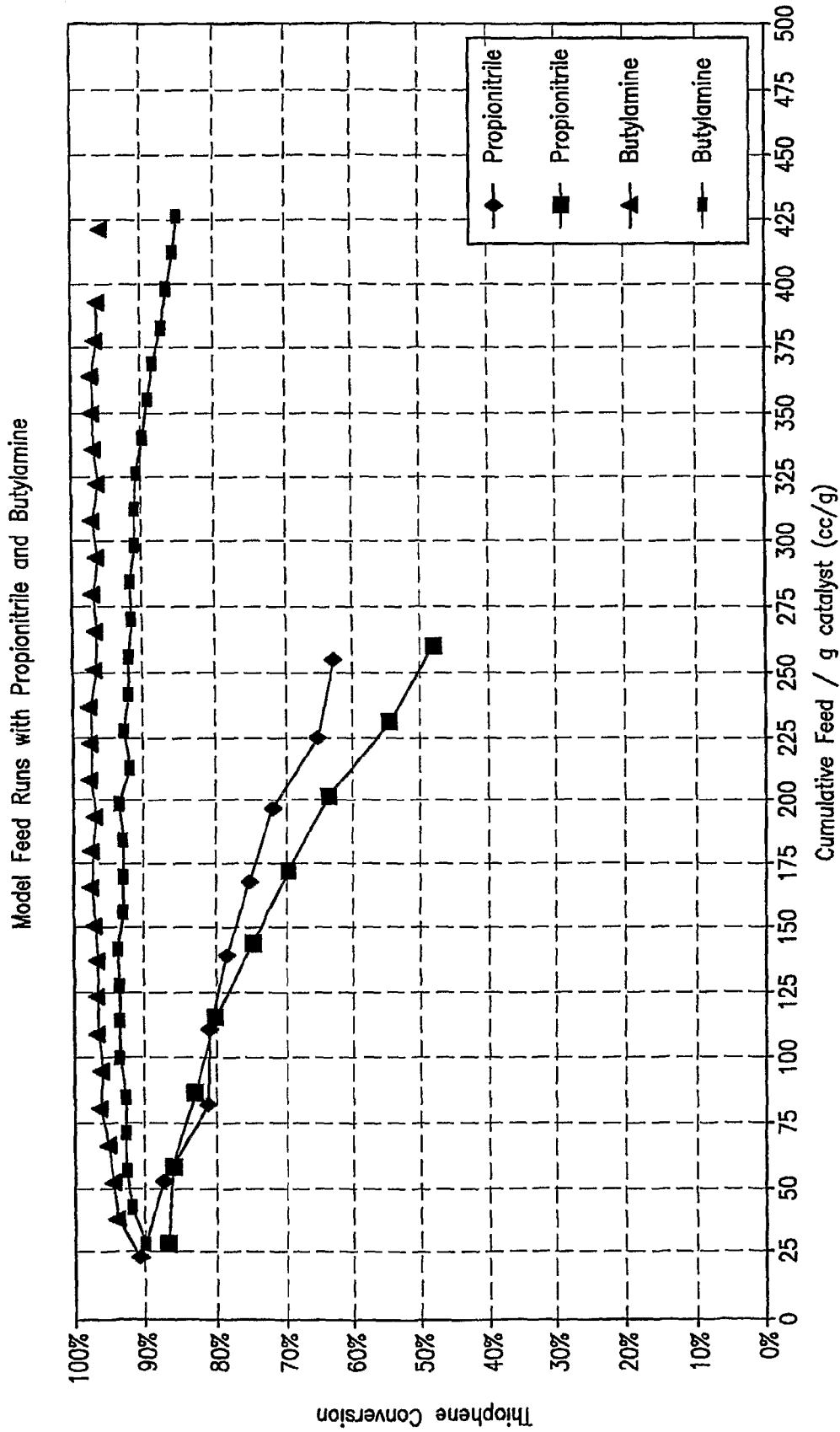
FIG. 1 plots thiophene conversion with various model feeds containing nitrogen compounds having different degrees of acidity.

Suitable feedstocks for used in this invention are derived from petroleum distillates which generally comprise most refinery streams consisting substantially of hydrocarbon compounds which are liquid at ambient conditions. Petroleum distillates are liquids which boil over either a broad or a narrow range of temperatures within the range from about 10° C. to about 345° C. However, such liquids are also encountered in the refining of products from coal liquefaction and the processing of oil shale or tar sands. These distillate feedstocks can range as high as 2.5 percent by weight elemental sulfur but generally range from about 0.1 percent by weight to about 0.9 percent by weight elemental sulfur. The higher sulfur distillate feedstocks are generally virgin distillates derived from high sulfur crude, coker distillates, and catalytic cycle oils from fluid catalytic cracking units processing relatively higher sulfur feedstocks. Nitrogen content of distillate feedstocks in the present invention is also generally a function of the nitrogen content of the crude oil, the hydrogenation capacity of a refinery per barrel of crude capacity, and the alternative dispositions of distillate hydrogenation feedstock components. The higher nitrogen distillate feedstocks are generally coker distillate and the catalytic cycle oils. These distillate feedstocks can have total nitrogen concentrations ranging as high as 2000 parts per million, but generally range from about 5 parts per million to about 900 parts per million.

Suitable refinery streams generally have an API gravity ranging from about 10° API to about 100° API, preferably from about 10° API to about 75 or 100° API, and more preferably from about 15° API to about 50° API for best results. These streams include, but are not limited to, fluid catalytic process naphtha, fluid or delayed process naphtha, light naphtha, hydrocracker naphtha, hydrotreating process naphthas, isomerate, and catalytic reformate, and combinations thereof. Catalytic reformate and catalytic cracking process naphthas can often be split into narrower boiling range streams such as light and heavy catalytic naphthas and light and heavy catalytic reformate, which can be specifically customized for use as a feedstock in accordance with the present invention. The preferred streams are light virgin naphtha, catalytic cracking naphthas including light and heavy catalytic cracking unit naphtha, catalytic reformate including light and heavy catalytic reformate and derivatives of such refinery hydrocarbon streams.

More suitable feedstocks for used in this invention include any of the various complex mixtures of hydrocarbons derived from refinery distillate steams which generally boil in a temperature range from about 60° C. to about 425° C. Generally such feedstock are comprised of a mixture of hydrocarbons, but contain a minor amount of sulfur-containing organic impurities including aromatic impurities such as thiophenic compounds and benzothiophenic compounds. Preferred feedstocks have an initial boiling point which is below about 79° C. and have a distillation endpoint which is about 345° C. or lower, and more preferably about 249° C. or lower. If desired, the feedstock can have a distillation endpoint of about 221° C. or lower.

It is also anticipated that one or more of the above distillate steams can be combined for use as a feedstock. In many cases performance of the refinery transportation fuel or blending components for refinery transportation fuel obtained from the various alternative feedstocks may be comparable. In these cases, logistics such as the volume availability of a stream, location of the nearest connection and short term economics may be determinative as to what stream is utilized.

Products of catalytic cracking are highly preferred feedstocks for use in this invention. Feedstocks of this type include liquids which boil below about 345° C.; such as light naphtha, heavy naphtha and light cycle oil. However, it will also be appreciated that the entire output of volatile products from a catalytic cracking process can be utilized as a feedstock in the subject invention. Catalytic cracking products are a desirable feedstock because they typically contain a relatively high olefin content, which usually makes it unnecessary to add any additional alkylating agent during the first alkylation stage of the invention. In addition to sulfur-containing organic compounds, such as mercaptans and sulfides, sulfur-containing aromatic compounds, such thiophene, benzothiophene and derivatives of thiophene and benzothiophene, are frequently a major component of the sulfur-containing impurities in catalytic cracking products, and such impurities are easily removed by means of the subject invention. For example, a typical light naphtha from the fluidized catalytic cracking of a petroleum derived gas oil can contain up to about 60 percent by weight of olefins and up to about 0.5 percent by weight of sulfur wherein most of the sulfur will be in the form of thiophenic and benzothiophenic compounds. A preferred feedstock for use in the practice of this invention will be comprised of catalytic cracking products and will be additionally comprised of at least 1 weight percent of olefins. A highly preferred feedstock will be comprised of catalytic cracking products and will be additionally comprised of at least 5 weight percent of olefins. Such feedstocks can be a portion of the volatile products from a catalytic cracking process which is isolated by distillation.

In the practice of this invention, the feedstock will contain sulfur-containing aromatic compounds as impurities. In one embodiment of the invention, the feedstock will contain both thiophenic and benzothiophenic compounds as impurities. If desired, at least about 50% or even more of these sulfur-containing aromatic compounds can be converted to higher boiling sulfur-containing material in the practice of this invention. In one embodiment of the invention, the feedstock will contain benzothiophene, and at least about 50% of the benzothiophene will be converted to higher boiling sulfur-containing material by alkylation and removed by fractionation.

Any acidic material which exhibits a capability to enhance the alkylation of sulfur-containing aromatic compounds by olefins or alcohols can be used as a catalyst in the thiophene alkylation zone of the present invention. Although liquid acids, such as sulfuric acid can be used, solid acidic catalysts are particularly desirable, and such solid acidic catalysts include liquid acids which are supported on a solid substrate. Solid acidic catalysts are generally preferred over liquid catalysts because of the ease with which the feed can be contacted with such a material. For example, feedstream can simply be passed through one or more fixed beds of solid particulate acidic catalyst at a suitable temperature. As desired, different acidic catalysts can be used in the various stages of the invention. For example, the severity of the alkylation conditions can be moderated in the alkylation step of the subsequent stage through the use of a less active catalyst, while a more active catalyst can be used in the alkylation step of the initial stage.

Catalysts useful in the practice of the invention include acidic materials such as catalysts comprised of acidic polymeric resins, supported acids, and acidic inorganic oxides. Suitable acidic polymeric resins include the polymeric sulfonic acid resins which are well-known in the art and are commercially available. Amberlyst® 35, a product produced by Rohm and Haas Co., is a typical example of such a material.

Supported acids which are useful as catalysts include but are not limited to Brönsted acids (examples include phosphoric acid, sulfuric acid, boric acid, HF, fluorosulfonic acid, trifluoro-methanesulfonic acid, and dihydroxyfluoroboric acid) and Lewis acids (examples include $BF_3$, $BCl_3$, $AlCl_3$, $AlBr_3$, $FeCl_2$, $FeCl_3$, $ZnCl_2$, $SbF_5$, $SbCl_5$ and combinations of $AlCl_3$ and HCl) which are supported on solids such as silica, alumina, silica-aluminas, zirconium oxide or clays.

Supported catalysts are typically prepared by combining the desired liquid acid with the desired support and drying. Supported catalysts which are prepared by combining a phosphoric acid with a support are highly preferred and are referred to herein as solid phosphoric acid catalysts. These catalysts are preferred because they are both highly effective and low in cost. U.S. Pat. No. 2,921,081 (Zimmerschied et al.), which is incorporated herein by reference in its entirety, discloses the preparation of solid phosphoric acid catalysts by combining a zirconium compound selected from the group consisting of zirconium oxide and the halides of zirconium with an acid selected from the group consisting of ortho-phosphoric acid, pyrophosphoric acid and triphosphoric acid. U.S. Pat. No. 2,120,702 (Ipatieff et al.), which is incorporated herein by reference in its entirety, discloses the preparation of a solid phosphoric acid catalyst by combining a phosphoric acid with a siliceous material.

British Patent No. 863,539, which is incorporated herein by reference in its entirety, also discloses the preparation of a solid phosphoric acid catalyst by depositing a phosphoric acid on a solid siliceous material such as diatomaceous earth or kieselguhr. When a solid phosphoric acid is prepared by depositing a phosphoric acid on kieselguhr, it is believed that the catalyst contains; (i) one or more free phosphoric acid, i.e., ortho-phosphoric acid, pyrophosphoric acid or triphosphoric acid, and (ii) silicon phosphates which are derived from the chemical reaction of the acid or acids with the kieselguhr. While the anhydrous silicon phosphates are believed to be inactive as an alkylation catalyst, it is also believed that they can be hydrolyzed to yield a mixture of ortho-phosphoric and polyphosphoric acids which are catalytically active. The precise composition of this mixture will depend upon the amount of water to which the catalyst is exposed.

In order to maintain a solid phosphoric acid alkylation catalyst at a satisfactory level of activity when it is used with a substantially anhydrous hydrocarbon feedstock, it is conventional practice to add a small amount of water or an alcohol, such as isopropyl alcohol, to the feedstock to maintain the catalyst at a satisfactory level of hydration. It is believed that the alcohol undergoes dehydration upon contact with the catalyst, and that the resulting water then acts to hydrate the catalyst. If the catalyst contains too little water, it tends to have a very high acidity which can lead to rapid deactivation as a consequence of coking and, in addition, the catalyst will not possess a good physical integrity. Further hydration of the catalyst serves to reduce its acidity and reduces its tendency toward rapid deactivation through coke formation. However, excessive hydration of such a catalyst can cause the catalyst to soften, physically agglomerate and create high pressure drops in fixed bed reactors. Accordingly, there is an optimum level of hydration for a solid phosphoric acid catalyst, and this level of hydration will be a function of the reaction conditions, the substrate, and the alkylating agent.

In preferred embodiments of the invention using solid phosphoric acid catalysts, a hydrating agent in an amount which exhibits a capability to enhance performance of the catalyst is required. Advantageously, the hydrating agent is at least one member of the group consisting of water and alkanols having from about 2 to about 5 carbon atoms. An amount of hydrating agent which provides a water concentration in the feedstock in the range from about 50 to about 1,000 parts per million is generally satisfactory. This water is conveniently provided in the form of an alcohol such as isopropyl alcohol.

Acidic inorganic oxides which are useful as catalysts include but are not limited to aluminas, silica-aluminas, natural and synthetic pillared clays, and natural and synthetic zeolites such as faujasites, mordenites, L, omega, X, Y, beta, and ZSM zeolites. Highly suitable zeolites include beta, Y, ZSM-3, ZSM-4, ZSM-5, ZSM-18, and ZSM-20. Desirably, the zeolites are incorporated into an inorganic oxide matrix material such as a silica-alumina. Indeed, equilibrium cracking catalyst can be used as the acid catalyst in the practice of this invention. Catalysts can comprise mixtures of different materials, such as a Lewis acid (examples include $BF_3$, $BCl_3$, $SbF_5$, and $AlCl_3$), a non-zeolitic solid inorganic oxide (such as silica, alumina and silica-alumina), and a large-pore crystalline molecular sieve (examples include zeolites, pillared clays and aluminophosphates).

A solid catalyst will desirably be in a physical form which will permit a rapid and effective contacting with the reactants in the process stage wherein it is used. Although the invention is not to be so limited, it is preferred that a solid catalyst be in particulate form wherein the largest dimension of the particles has an average value which is in the range from about 0.1 mm to about 2 cm. For example, substantially spherical beads of catalyst can be used which have an average diameter from about 0.1 mm to about 2 cm. Alternatively, the catalyst can be used in the form of rods which have a diameter in the range from about 0.1 mm to about 1 cm and a length in the range from about 0.2 mm to about 2 cm.

As stated previously, feedstocks used in the practice of this invention will contain nitrogen-containing organic compounds as impurities in addition to the sulfur-containing organic impurities. Many of the typical nitrogen-containing impurities are organic bases and, in some instances, can cause deactivation of the acidic catalyst or catalysts of the subject invention. It has now been discovered that the most deleterious nitrogen-containing organic molecules catalyst poisons are the non-basic nitrogen-containing organic molecules.

It has been discovered that the typical commercial feeds used in a thiophene alkylation process will contain a majority, often greater that 75 mol % of non-basic, i.e. either neutral or slighty acidic nitrogen compounds. These compounds include acetonitriles, propionitriles, butyronitriles, and pyrroles.

Without wishing to be bound by theory, it is believed that the non-basic nitrogen compounds are converted to basic compounds at the acid catalyst active sites. These non-basic nitrogen compounds were generally not removed by acid wash steps, water wash steps or guard bed steps using for instance a Lewis acid adsorbent guard bed which would remove basic nitrogen compounds prior to exposure to the acid catalyst.

It is believed that the non-basic nitrogen compounds selectively poison the active catalyst sites on the acid catalyst since these are the sites that convert the non-basic nitrogen compounds to basic nitrogen compounds.

Typically a light to middle fluidized catalytic cracking gasoline feedstream can have 10-25 ppmw non-basic nitrogen compounds whereas a heavier feed can have in excess of non-basic 50 ppmw nitrogen compounds.

In accordance with the process of the present invention these non-basic nitrogen compounds need to be removed and can be removed by the use of a combination of a base wash followed by an acid wash; an adsorbent or a combination of adsorbents that can be regenerated; or an acid material that preferentially reacts with non-basic nitrogen to form basic nitrogen compounds which can then be adsorbed. A combination of the above-three mentioned processes can also be used to remove non-basic nitrogen compounds. In accordance with the invention, the base wash-acid wash combination can be carried out at temperatures ranging from about 0 to about 100 degrees C. and preferably from about 20 to about 50 degrees C., and pressures can range from about 0 to about 100 psig, preferably from about 1 to about 25 psig.

Suitable base solutions include inorganic bases such as sodium hydroxide or potassium hydroxide with base concentrations in the range of about 5 to about 50% (wt), preferably from about 10 to about 20% (wt). The base wash can be done in 1 to 3 contact stages, most preferably 1 stage of contact. The base solution is recirculated to provide a contact ratio of between 10-100 volumes of solution to volume of oil feed, most preferably a ratio of about 50 to about 100 volumes solution to volume of feed.

Suitable acid solutions include inorganic acids such as sulfuric acid with acid concentrations in the range of about 5 to about 25% (wt), preferably from about 10 to about 20% (wt). Acid wash can be done in 1 to 3 contact stages, most preferably 1 stage of contact. The acid solution is recirculated to provide a contact ratio of between 10-100 volumes solution: oil feed, most preferably 50-100 volumes solution to volume oil feed.

The base wash must be done first, followed by the acid wash, to protect the acidic catalyst from any base carryover from the base wash step.

In accordance with the present invention, effective non-basic nitrogen compound adsorbents include alkaline or alkaline earth faujasite type zeolites, or partially exchanged alkaline or alkaline earth faujasite zeolites with $H^+$ or transition metals of Groups IB, IIB, IVB, VIII, crystalline, magnesium silicates, alkaline exchanged crystalline magnesium silicates or mixtures of all of the above.

The adsorbent can also be a physical mixture of sepiolite, Na—X, and Na—Y zeolites where these components are present in amounts ranging from 5 to 95% (vol) each.

The adsorption can be carried at temperatures from about 0 to about 100 degrees C., preferably 20 to about 40 degrees C., and pressures can range from about 0 to about 300 psig, and preferably from about 100 to about 150 psig. Feed to adsorbent weigh hourly space velocity ("WHSV") can range from about 0.5 to about 50 hour$^{-1}$, and most preferably from about 10 to about 15 hr$^{-1}$.

The amount of absorbent can be an amount sufficient to run between about 0.5 and about 15 days between regenerations, more preferably from about 1 to about 5 days between regenerations.

The regeneration of the spent absorbent can be achieved either by thermal treatment, solvent wash, or pressure swing desorption.

These methods include high temperature oxidation at conditions including temperatures of from about 100 to about 1000 degrees C., preferably from about 100 to about 500 degrees C. and pressures of from about 0 to about 100 psia, and preferably from about 0 to about 50 psia in the presence of an oxygen containing gas.

High temperature pyrolisis conditions include temperatures from about 100 to about 1000 degrees C., and preferably from about 100 to about 500 degrees C. and pressures from 0 to about 100 psia, and preferably from about 0 to about 50 psia.

High temperature hydrotreatment conditions include temperatures from about 500 to about 700 degrees C. and pressures from about 25 to about 40 atmospheres pressure in the presence of a hydrogen-containing gas.

For a solvent wash an effective solvent is toluene, as it is refinery based. It is also believed many other refinery oil based streams will also be effective as regeneration solvents. The solvent regeneration is generally carried out under at conditions including temperatures from about 50 to about 400 degrees F. and from about 0 to about 300 psig pressure, and more preferably from about 50 to about 150 degrees F. and 0 to about 50 psig.

Additionally a pressure swing operation can be carried out to regenerate the catalyst at conditions including temperatures from about 100 to about 500 degrees F. and pressures from about 0 to about 50 psia pressure using a sweeping gas such as nitrogen.

Suitable methods which remove the basic nitrogen-containing impurities, have heretofore typically involved treatment with an acidic material. Such methods include procedures such as washing with an aqueous solution of an acid and the use of a guard bed which is positioned in front of the acidic catalyst. Examples of effective guard beds include but are not limited to A-zeolite, Y-zeolite, L-zeolite, mordenite, fluorided alumina, fresh cracking catalyst, equilibrium cracking catalyst and acidic polymeric resins. Where a guard bed technique is employed, it is often desirable to use two guard beds in such a manner that one guard bed can be regenerated while the other is being used to pretreat the feedstock and protect the acidic catalyst. If a cracking catalyst is utilized to remove basic nitrogen-containing impurities, catalyst can be regenerated in the regenerator of a catalytic cracking unit when it has become deactivated with respect to its ability to remove such impurities. If an acid wash is used to remove basic nitrogen-containing compounds, the feedstock will be treated with an aqueous solution of a suitable acid. Suitable acids for this use include but are not limited to hydrochloric acid, sulfuric acid and acetic acid. The concentration of acid in the aqueous solution is not critical, but is conveniently chosen to be in the range from about 0.1 percent to about 30 percent by weight. For example, a 2 percent by weight solution of sulfuric acid in water can be used to remove basic nitrogen containing compounds from a heavy naphtha from a catalytic cracking process.

In the practice of this invention after removal of the non-basic nitrogen compounds, the feed to the alkylation step is contacted with the acidic catalyst at a temperature and for a period of time which are effective to result in the desired degree of conversion of selected sulfur-containing organic impurities to a higher boiling sulfur-containing material. The contacting temperature will be desirably in excess of about 50° C., preferably in excess of 85° C., and more preferably in excess of 100° C. The contacting will generally be carried out at a temperature in the range from about 50° C. to about 260° C., preferably from about 85° C. to about 220° C., and more preferably from about 100° C. to about 200° C. It will be appreciated, of course, that the optimum temperature will be a function of the acidic catalyst used, the alkylating agent or agents selected, the concentration of alkylating agent or agents, and the nature of the sulfur-containing aromatic impurities that are to be removed.

The effluent from the acid catalyst contacting step can then be fractionated into at least one low-boiling fraction consisting of a sulfur-lean fraction and a high boiling fraction which contains a portion of the higher boiling sulfur-containing materials as taught for instance in U.S. Pat. No. 6,736,963 the teachings of which are incorporated herein by reference.

This invention is an integrated, multistage process for concentrating the sulfur-containing aromatic impurities of a hydrocarbon feedstock into a relatively small volume of high boiling material. As a result of this concentration, the sulfur can be disposed of more easily and at lower cost, and any conventional method can be used for this disposal. For example, this material can be blended into heavy fuels where the sulfur content will be less objectionable. Alternatively, it can be efficiently hydrotreated at relatively low cost because of its reduced volume relative to that of the original feedstock.

In another embodiment it is believed that the removal of non-basic nitrogen compounds by the adsorbents of the present invention will also enhance the performance of other processes using solid acid catalysts such as the catalytic condensation or polymerization process used to produce polygasoline from light olefins.

A variety of commercial chemical and petrochemical processes involve the condensation reaction of an olefin or a mixture of olefins over an acid catalyst to form higher molecular weight products. This process is referred to herein as a polymerization process, and the products can be either low molecular weight oligomers or high molecular weight polymers. Oligomers are formed by the condensation of 2, 3 or 4 olefin molecules with each other, while polymers are formed by the condensation of 5 or more olefin molecules with each other. As used herein, the term "polymerization" is used to refer to a process for the formation of oligomers and/or polymers.

Low molecular weight olefins (such as propene, 2-methylpropene, 1-butene and 2-butene) can be converted by polymerization over a solid acid catalyst (such as a solid phosphoric acid catalyst) to a product which is comprised of oligomers and is of value as a high-octane gasoline blending stock and as a starting material for the production of chemical intermediates and end-products which include alcohols, detergents and plastics. Such a process is typically carried out over a fixed-bed of solid acid catalyst and at elevated temperatures and pressures.

Such polymerization processes are described in greater detail in U.S. Pat. No. 5,932,778, the teachings of which are incorporated herein by reference.

Example 1

FIG. 1 shows a plot of the results of four pilot plant runs using an acid catalyzed thiophene alkylation process. More specifically, the runs were carried out with model feeds two of which contained the non-basic nitrogen compound propionitrile and two of which contained the basic nitrogen compound butylamine. Thiophene conversion is plotted on the Y axis in molar percentage of thiophene converted as a function of cumulative feed charged to the catalyst as plotted on the X axis.

Figure 2:
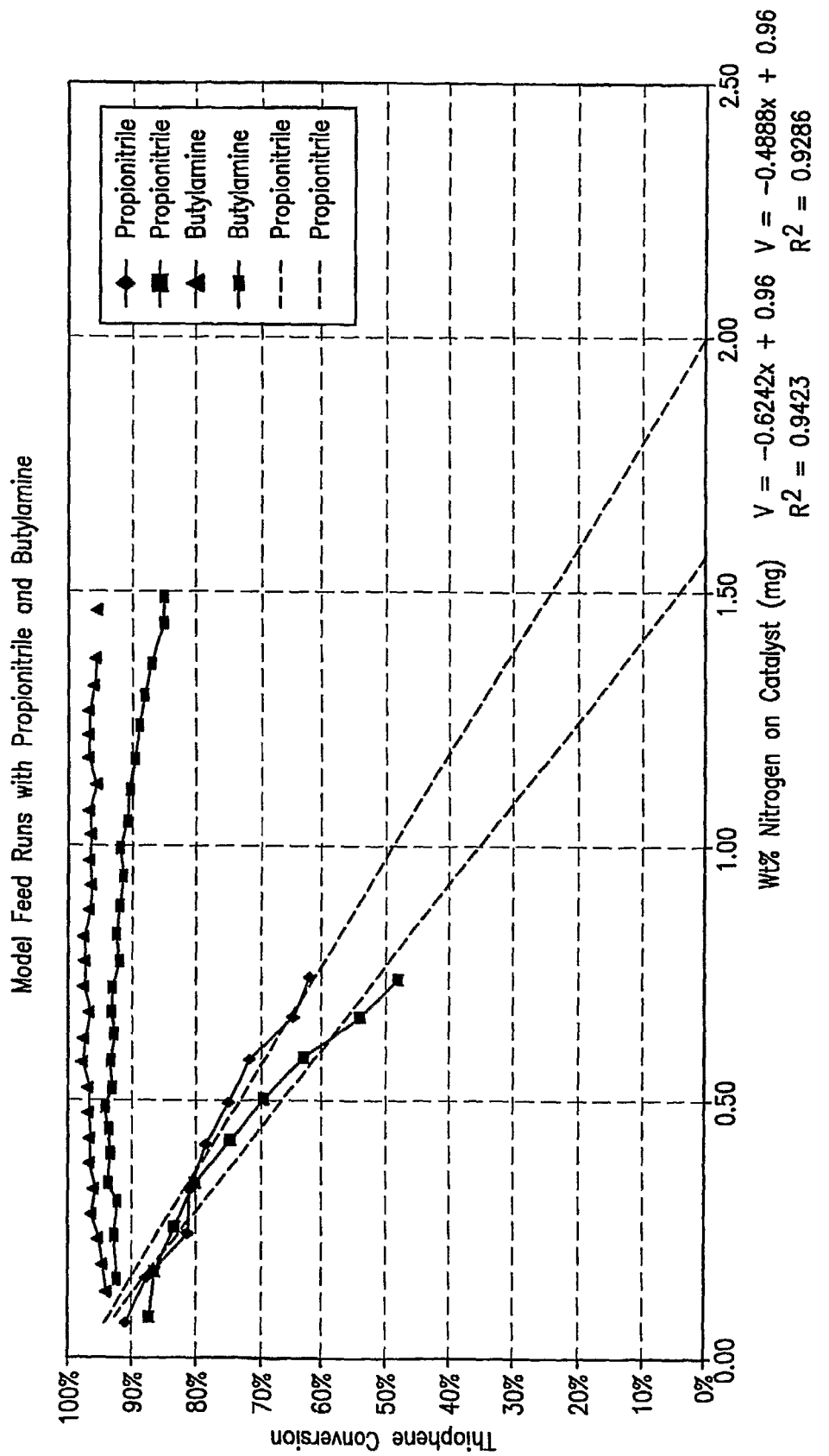
FIG. 2 plots thiophene conversion for the runs plotted in FIG. 1 as a function of nitrogen adsorbed onto the catalyst.

FIG. 2 shows the same plot of thiophene conversion as a function of wt. % nitrogen on the catalyst.

As can be readily observed from an inspection of the plot, the presence of non-basic nitrogen compounds in the feed results in a marked decrease of thiophene conversion activity versus feeds having only basic nitrogen compounds present.

The compositions of the model feeds used in the runs depicted in FIGS. 1 and 2 are set forth below in Table 1.

TABLE 1

Model Feed Inspections

| | Propionitrile Runs | Butylamine Runs |
|---|---|---|
| 2-Methyl-2-Butene | 20% weight | 20% weight |
| 4-Methyl-1-Pentene | 20% weight | 20% weight |
| Hexane | 60% weight | 60% weight |
| Thiophene | 160 ppm | 153 ppmwt |
| 2-Methyl Thiophene | 160 ppm | 153 ppmwt |
| 3-Methyl Thiophene | 160 ppm | 150 ppmwt |
| Propionitrile | 45 ppm (as nitrogen) | 51.6 ppm (as nitrogen) |

The pilot plant used to generate the data in FIGS. 1 and 2 was loaded with 54 cc of a solid phosphoric acid catalyst (C84-5-02 supplied by Süd Chemie, Inc. Louisville, Ky., USA) which was crushed to a Tyler screen mesh size of −12+20 (USA Standard Testing Sieve by W.S. Tyler). The pilot-scale reactor consisted of a 34 inch length of ¾ O.D.× 0.620 inch I.D.×0.065 inch wall Stainless Steel tubing. The reactor temperatures were maintained by four electrically heated sections of the reactor wall inside an insulated furnace box. The temperatures of these sections were controlled by a programmable computer with the use of single point thermocouples on each of the reactor wall sections. There was also an ⅛ inch O.D. stainless steel thermowell that run through the middle of the reactor from the top. This thermowell housed the multi-point thermocouple (3 point multi-point thermocouple with 2" spacings) for monitoring temperatures throughout the reactor.

The pilot plant reactor consisted of a preheat zone (temperature zone 1) which was filled with alumina chips, sieved to a Tyler screen mesh size of −12+20 (USA Standard Testing Sieve by W.S. Tyler). The second and third heated zones were loaded with 54 cc of a solid phosphoric acid catalyst (C84-5-02 supplied by Sud Chemie, Inc. Louisville, Ky., USA) which was crushed to a Tyler screen mesh size of −12+20 (USA Standard Testing Sieve by W.S. Tyler). The remainder of the reactor (temperature zone 4) was filled with alumina chips, sieved to a Tyler screen mesh size of −12+20 (USA Standard Testing Sieve by W.S. Tyler) as a cooldown zone and to support the catalyst.

The process feed stream was introduced into the reactor using a precision syringe metering pump (ISCO). The feed was preheated to the reaction temperature in the reactor preheat zone and measured along the centerline by thermocouples in various positions, and the heating zones were adjusted accordingly. The liquid product from the reactor was passed into a cooled high pressure separator/receiver where nitrogen was used to maintain the outlet pressure of the reactor at the desired operating pressure. Pressure was controlled by a Badger Research control valve on the offgas from the separator/receiver. Liquid samples were drained from the high pressure receiver/separator and analyzed by multi-column gas chromatograph for sulfur specification, nitrogen specification, and olefin specification.

For these experiments, 54 cc of catalyst were charged to the reactor. Feed flow rates were operated to achieve a liquid hydraulic space velocity (standard volume of feed in cc/hour divided by charged volume of catalyst in cc) of 3.0 hr-1. The reaction zone temperature was maintained at 350 F+/−5° F. and 400 psig+/−10 psig.

The conditions used for each run included:

| LHSV | $3.0\ hr^{-1}$ |
|---|---|
| Pressure | 400 psig |
| Temperature | 350° F. |

The following Table 2 below shows the actual data plotted in FIGS. 1 and 2.

TABLE 2

| Hours on Line (hrs) | Thiophene Conversion (%) | Nitrogen On Catalyst (wt %) | Cumulative Feed/Catalyst (cc feed/g cat) |
|---|---|---|---|
| Propionitrile Run #1 | | | |
| 0.0 | 0 | 0.00% | 0.0 |
| 6.7 | 90.8% | 0.07% | 24.0 |
| 14.7 | 87.6% | 0.16% | 52.7 |
| 22.7 | 81.3% | 0.24% | 81.5 |
| 30.7 | 80.8% | 0.33% | 110.3 |
| 38.7 | 78.5% | 0.42% | 139.0 |
| 46.7 | 75.1% | 0.50% | 167.8 |
| 54.7 | 71.6% | 0.58% | 196.5 |
| 62.7 | 64.7% | 0.67% | 225.3 |
| 70.7 | 62.2% | 0.74% | 254.1 |
| Propionitrile Run #2 | | | |
| 0.0 | 0 | 0.00% | 0.0 |
| 8.0 | 86.8% | 0.09% | 28.8 |
| 16.0 | 86.3% | 0.17% | 57.6 |
| 24.0 | 83.0% | 0.26% | 86.3 |
| 32.0 | 80.1% | 0.34% | 115.1 |
| 40.0 | 74.6% | 0.43% | 143.9 |
| 48.0 | 69.1% | 0.51% | 172.7 |
| 56.0 | 63.1% | 0.59% | 201.5 |
| 64.0 | 54.0% | 0.67% | 230.3 |
| 72.0 | 47.7% | 0.74% | 259.0 |
| Butylamine Run #1 | | | |
| 10.7 | 94.1% | 0.13% | 37.8 |
| 14.7 | 94.8% | 0.18% | 52.0 |
| 18.7 | 95.4% | 0.23% | 66.2 |
| 22.7 | 96.6% | 0.28% | 80.4 |
| 26.7 | 96.2% | 0.33% | 94.6 |
| 30.7 | 96.8% | 0.38% | 108.8 |
| 34.7 | 96.7% | 0.43% | 123.0 |
| 38.7 | 96.9% | 0.48% | 137.2 |
| 42.7 | 97.1% | 0.53% | 151.4 |
| 46.7 | 97.6% | 0.58% | 165.5 |
| 50.7 | 97.7% | 0.63% | 179.7 |
| 54.7 | 97.0% | 0.68% | 193.9 |
| 58.7 | 97.5% | 0.73% | 208.1 |
| 62.7 | 97.6% | 0.77% | 222.3 |
| 66.7 | 97.5% | 0.82% | 236.5 |
| 70.7 | 96.9% | 0.87% | 250.7 |
| 74.7 | 96.7% | 0.92% | 264.9 |
| 78.7 | 96.8% | 0.97% | 279.1 |
| 82.7 | 96.3% | 1.02% | 293.3 |
| 86.7 | 96.8% | 1.07% | 307.4 |
| 90.7 | 96.0% | 1.12% | 321.6 |
| 94.7 | 96.8% | 1.17% | 335.8 |
| 98.7 | 96.7% | 1.22% | 350.0 |
| 102.7 | 96.8% | 1.27% | 364.2 |
| 106.7 | 96.1% | 1.32% | 378.4 |
| 110.7 | 96.1% | 1.37% | 392.6 |
| 114.7 | 96.1% | 1.42% | 406.8 |
| 118.7 | 95.5% | 1.47% | 421.0 |
| Butylamine Run #2 | | | |
| 8.0 | 90.2% | 0.10% | 28.4 |
| 12.0 | 92.1% | 0.15% | 42.6 |
| 16.0 | 92.9% | 0.20% | 56.7 |
| 20.0 | 92.8% | 0.25% | 70.9 |
| 24.0 | 92.9% | 0.30% | 85.1 |
| 28.0 | 93.6% | 0.35% | 99.3 |

TABLE 2-continued

| Hours on Line (hrs) | Thiophene Conversion (%) | Nitrogen On Catalyst (wt %) | Cumulative Feed/Catalyst (cc feed/g cat) |
|---|---|---|---|
| 32.0 | 93.5% | 0.40% | 113.5 |
| 36.0 | 93.6% | 0.44% | 127.7 |
| 40.0 | 93.8% | 0.49% | 141.9 |
| 44.0 | 93.1% | 0.54% | 156.1 |
| 48.0 | 93.1% | 0.59% | 170.2 |
| 52.0 | 92.9% | 0.64% | 184.4 |
| 56.0 | 93.3% | 0.69% | 198.8 |
| 60.0 | 92.0% | 0.74% | 212.8 |
| 64.0 | 92.6% | 0.79% | 227.0 |
| 68.0 | 92.1% | 0.84% | 241.2 |
| 72.0 | 92.0% | 0.89% | 255.4 |
| 76.0 | 91.6% | 0.94% | 269.6 |
| 80.0 | 91.7% | 0.99% | 283.7 |
| 84.0 | 91.1% | 1.04% | 297.9 |
| 88.0 | 90.9% | 1.09% | 312.1 |
| 92.0 | 90.3% | 1.14% | 326.3 |
| 96.0 | 89.7% | 1.19% | 340.5 |
| 100.0 | 89.0% | 1.24% | 354.7 |
| 104.0 | 88.2% | 1.29% | 368.9 |
| 108.0 | 87.1% | 1.33% | 383.1 |
| 112.0 | 86.2% | 1.38% | 397.2 |
| 116.0 | 85.2% | 1.43% | 411.4 |
| 120.0 | 84.8% | 1.48% | 425.6 |

Example 2

Figure 3:
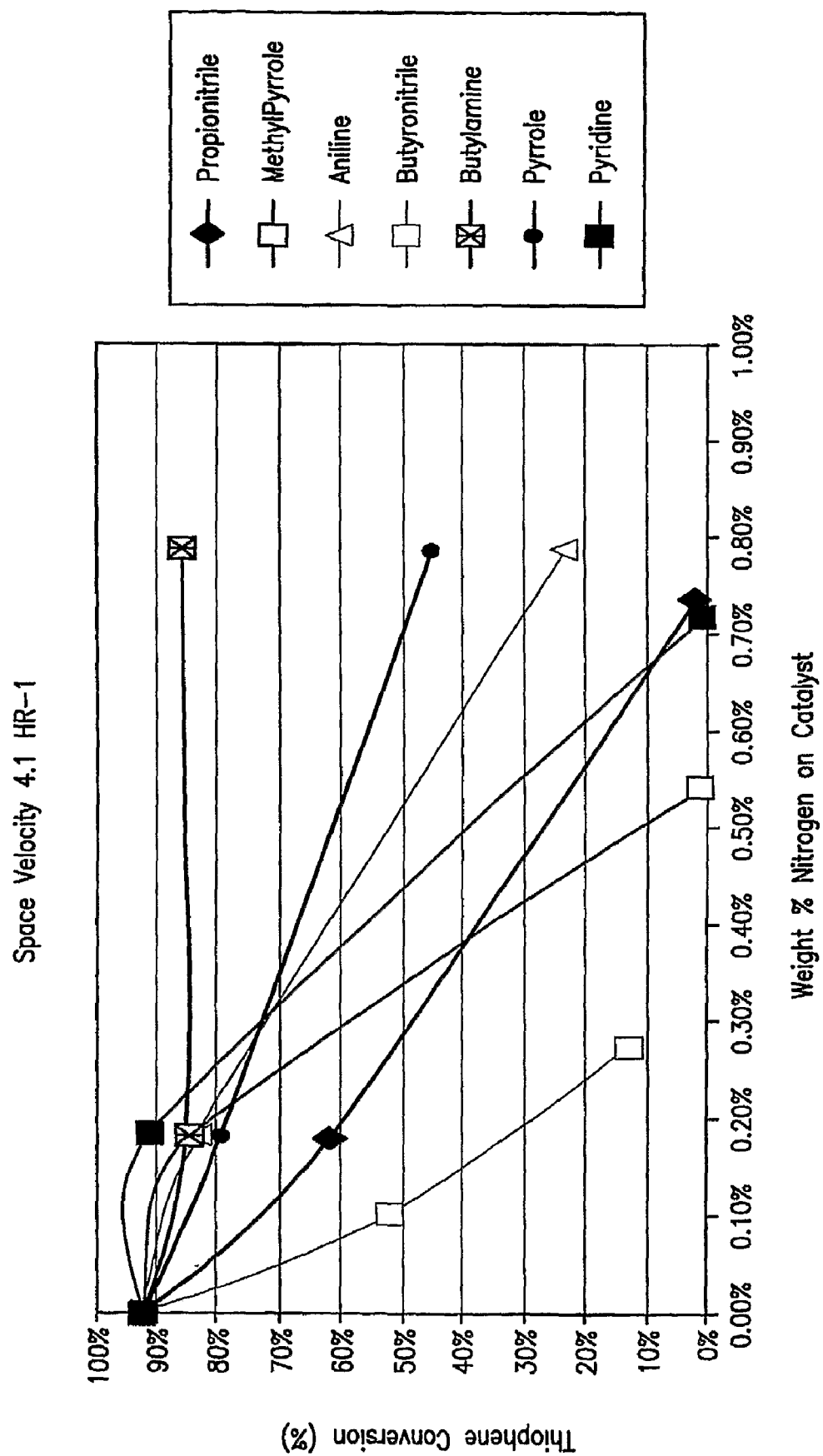
FIG. 3 plots thiophene conversion as a function of weight percent nitrogen deposited on the catalyst for additional feeds containing nitrogen compounds having varying degrees of acidity.

FIG. 3 show a plot of the results of additional pilot plant runs using an acid catalyzed thiophene alkylation process. More specifically, the runs were carried out with model feeds which contained 80 ppmw of seven nitrogen compounds, both non-basic and basic nitrogen compounds. In FIG. 3, thiophene conversion is plotted on the Y axis in molar percentage of thiophene converted as a function of weight % nitrogen adsorbed on the catalyst. An inspection of the plot clearly shows that the more basic the nitrogen compound, the flatter the curve; i.e. the less the catalyst deactivation. The presence of non-basic nitrogen compounds in the feed results in a marked decrease of thiophene conversion activity versus feeds having only basic nitrogen compounds present.

Preliminary experimentation was conducted to determine a space velocity that would yield a thiophene conversion of ~95% using the based feed (50% 1-hexene, 50% n-heptane, 200 ppm S as thiophene) which would allow the experimental program to clearly and quickly determine the poisoning effect of the nitrogen contaminants in the feed. Based on this preliminary work, a space velocity (WHSV) of 4.1 hr-1 was chosen for the remainder of the experiments.

For the experiments carried out in the present example, the following base feed was utilized:
- 50% 1-hexene
- 50% n-heptane
- 200 ppm Sulfur (as thiophene)
- 80 ppmw N (as various nitrogen contaminants)

The following nitrogen contaminants were evaluated as added to the base feed:
- None
- Propionitrile (non-basic)
- Methyl Pyrrole (non-basic)
- Aniline (Basic)
- Butylamine (basic)
- Pyrrole (non-basic)
- Pyridine (basic)
- Butyronitrile (non-basic)

More specifically, the results show that the various nitrogen compounds can be classified regarding their poisoning impact on the acid catalyzed thiophene alkylation process process into: (1) highly poisoning compounds for the process such as pyridine, methylpyrrole, propionitrile and butyronitrile; (ii) moderately poisoning compounds for the process—aniline and pyrrole, and (iii) low level poisoning compounds for the thiophene alkylation process—butylamine. Under the reaction conditions employed in the present example, most of the nitrogen compounds were totally retained on the catalyst during the first days of reaction. For longer times on-stream nitrogen adsorption decreased slightly, especially for nitrile compounds.

The solid phosphoric acid catalyst used in the pilot plant runs of the present example was a commercially available catalyst designated as C-84-05 obtained from Süd Chemie Inc. Louisville, Ky., USA. The pilot plant was loaded with 300 mg of a solid phosphoric acid catalyst which was crushed to a Tyler screen mesh size of 0.4-0.6 mm. The catalyst was dried under nitrogen flow for 2 hours at 200° C. prior to use. The pilot plant consisted of parallel fixed bed reactors, each capable of holding between 50 to 1000 mg of catalyst. The pilot plant design was similar to the design described in example 1 above. The reactors were operated in a downflow operation.

The conditions used for each run included:

| LHSV | 4.1 hr$^{-1}$ |
|---|---|
| Pressure | 400 psig |
| Temperature | 180° C. |

The data plotted in FIG. 3 are set forth below in Table 3:

TABLE 3

| N Compound | @ 8 Hours % Nitrogen Absorption | @ 8 Hours Nitrogen on Catalyst (%) | @ 8 Hours Thiophene Conversion (% | @ 32 Hours % Nitrogen Absorption | Average % Nitrogen Absorption | @ 32 Hours Nitrogen on Catalyst (%) | @ 32 Hours Thiophene Conversion (%) |
|---|---|---|---|---|---|---|---|
| | | 0.00 | 92% | | | | 92% |
| Propionitrile | 98% | 0.18% | 62% | 89% | 94% | 0.74% | 2% |
| MethylPyrrole | 100% | 0.18% | 84% | 38% | 69% | 0.54% | 1% |
| Aniline | 100% | 0.18% | 83% | 100% | 100% | 0.79% | 23% |
| Butylamine | 100% | 0.18% | 85% | 100% | 100% | 0.79% | 86% |
| Pyrrole | 100% | 0.18% | 79% | 100% | 100% | 0.79% | 45% |
| Pyridine | 100% | 0.18% | 91% | 82% | 91% | 0.72% | 1% |
| Butyronitrile | 55% | 0.10% | 52% | 15% | 35% | 0.28% | 13% |

Example 3

Table 4 sets out the feed inspections for a commercial acid catalyzed thiophene alkylation process feedstock that contains all of the indigenous non-basic nitrogen compounds and for the feed treated to remove nitrogen, first by acid washing and second by resin treatment. This commercial feed is a light cut range fluidized catalytic cracking (FCC) gasoline cut. This feed, typical of the type of feed processed by an acid catalyzed thiophene alkylation process unit, can be seen to contain a wide variety of nitrogen compounds. These nitrogen compounds can be separated into 3 general classifications: (1) basic nitrogen species including butylamine, hexamine, and pyridine; (2) neutral compounds including acetonitrile, propionitrile, and butyronitrile; and (3) somewhat acidic nitrogen compounds including pyrroles. The acid wash principally removed the basic nitrogen compounds, leaving behind the majority of the non-basic nitrogen compounds. In particular, the butyronitrile has limited solubility in water and tends not to be removed by acid washing. A treatment of the feed with a resin was able to remove additional levels of the non-basic nitrogen compounds.

TABLE 4

Pilot Plant Treated Standard Feed Nitrogen Speciation

| | Commercial Feed Nitrogen (ppm) | Acid Washed Nitrogen (ppm) | Resin Treated Nitrogen (ppm) |
|---|---|---|---|
| Total Nitrogen (ASTM D4629) | 21.0 | 8.4 | 3.9 |
| ACETONITRILE | 0.29 | | |
| PROPIONITRILE | 6.35 | 5.79 | 0.37 |
| ISOBUTYRONITRILE | 0.65 | 0.41 | 0.31 |
| <unknown> | 0.16 | 0.13 | |
| BUTYLAMINE | 0.16 | 0.16 | |
| BUTYRONITRILE | 1.42 | 1.13 | 0.55 |
| <unknown> | 0.22 | | |
| <unknown> | 0.18 | 0.20 | 0.16 |
| <unknown> | 0.24 | 0.25 | 0.19 |
| <unknown> | 0.07 | 0.07 | |
| <unknown> | 0.13 | 0.14 | |
| PYRIDINE | 0.42 | | |
| 1-METHYLPYRROLE | 0.10 | | |
| PYRROLE | 2.83 | 0.18 | 0.24 |
| DIMETHYLFORMAMIDE | 0.48 | 0.38 | 0.17 |
| VALERONITRILE | 0.10 | 0.01 | |
| <unknown> | 0.38 | 0.35 | 0.13 |
| <unknown> | 0.64 | 0.11 | 0.09 |
| <unknown> | 0.13 | | |
| <unknown> | 0.20 | | |
| <unknown> | 0.22 | 0.08 | |
| 2-METHYLPYRIDINE | 0.41 | | |
| <unknown> | 0.12 | 0.09 | |
| <unknown> | 1.82 | | |
| HEXYLAMINE | 1.29 | | |
| 3-METHYLPYRIDINE | 0.31 | | |
| <unknown> | 0.33 | 0.12 | |
| <unknown> | 0.15 | | |

Figure 4:
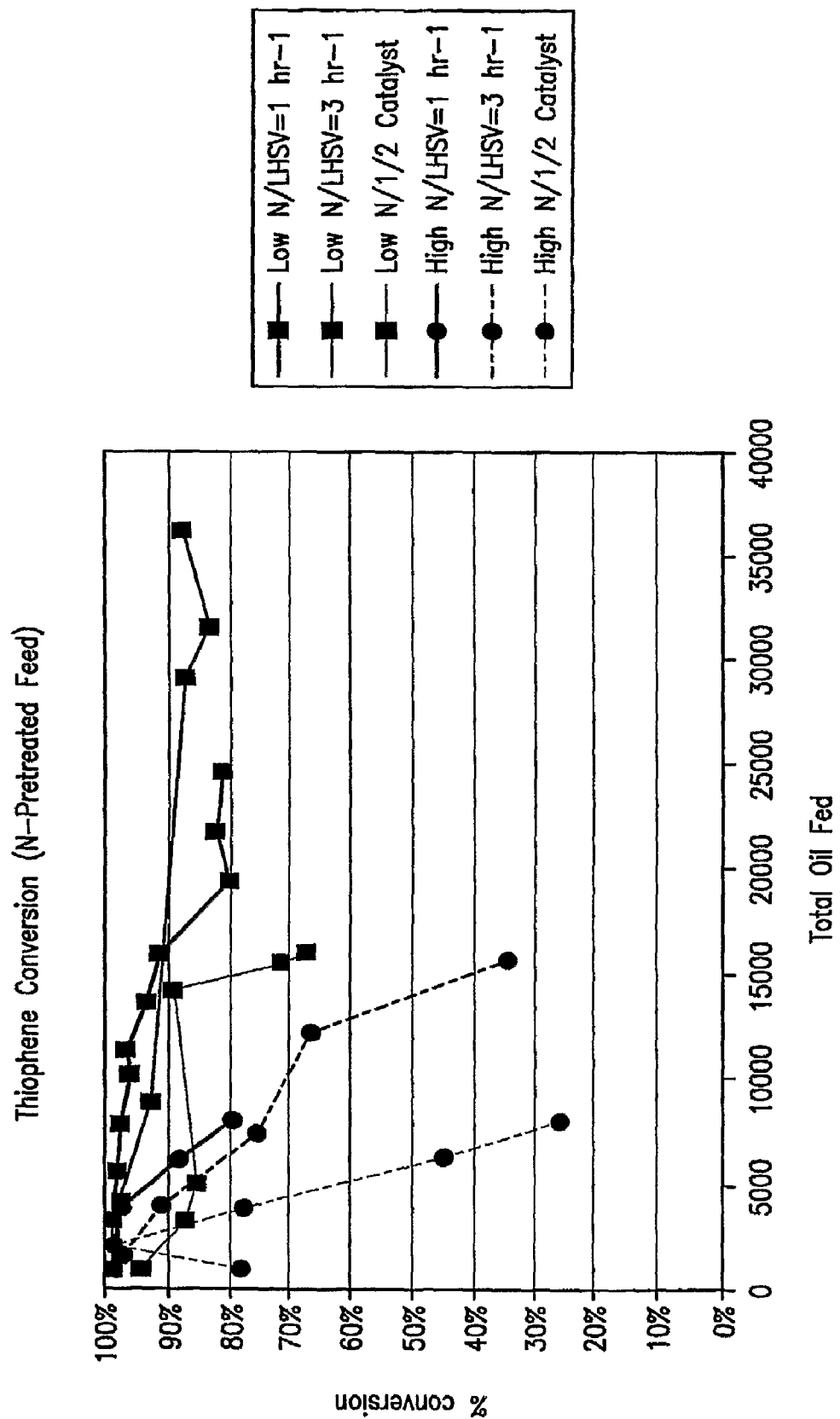
FIGS. 4, 5 and 6 depict plots that show thiophene conversion for various feeds that are untreated and treated at various different reaction conditions.
Figure 5:
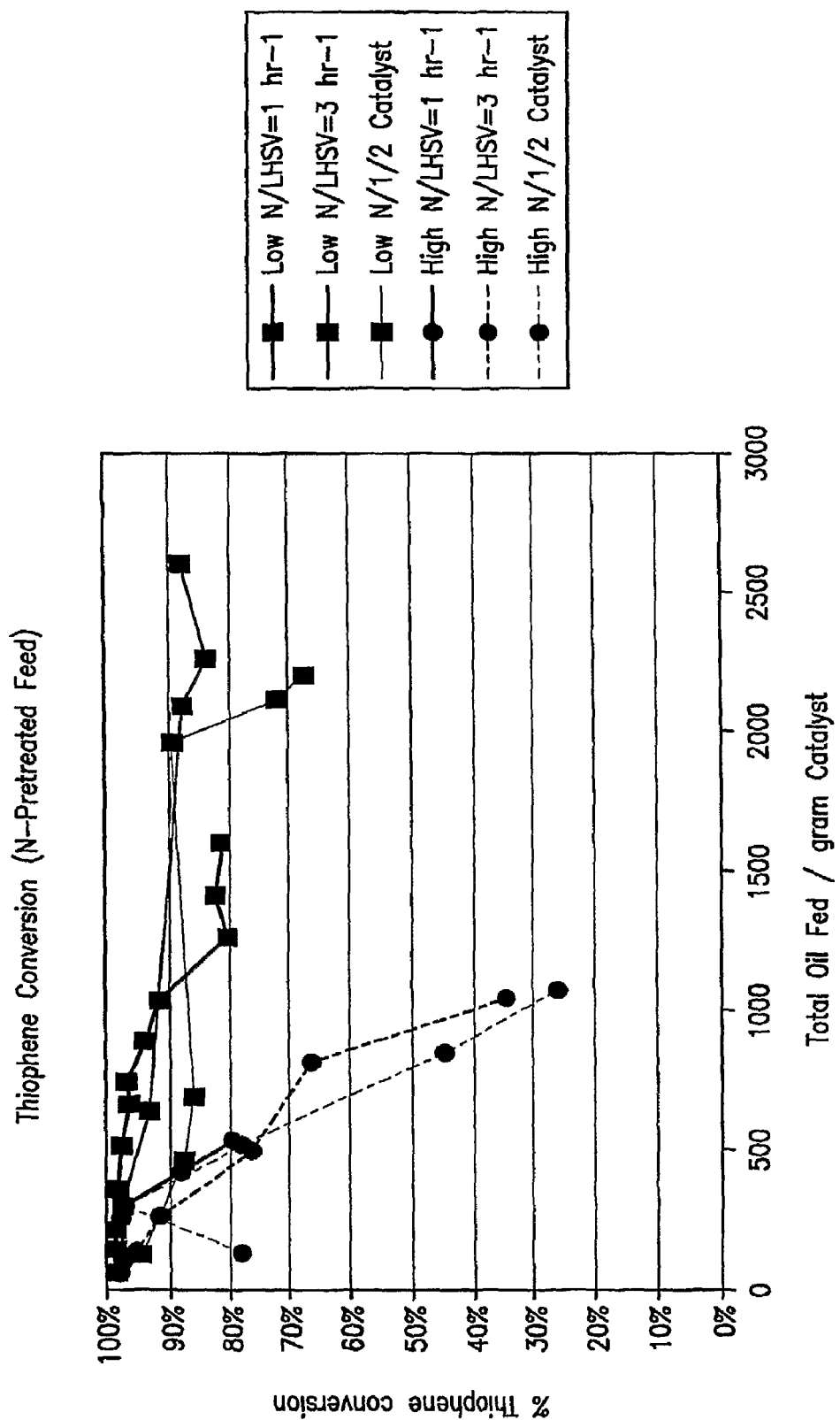
Figure 6:
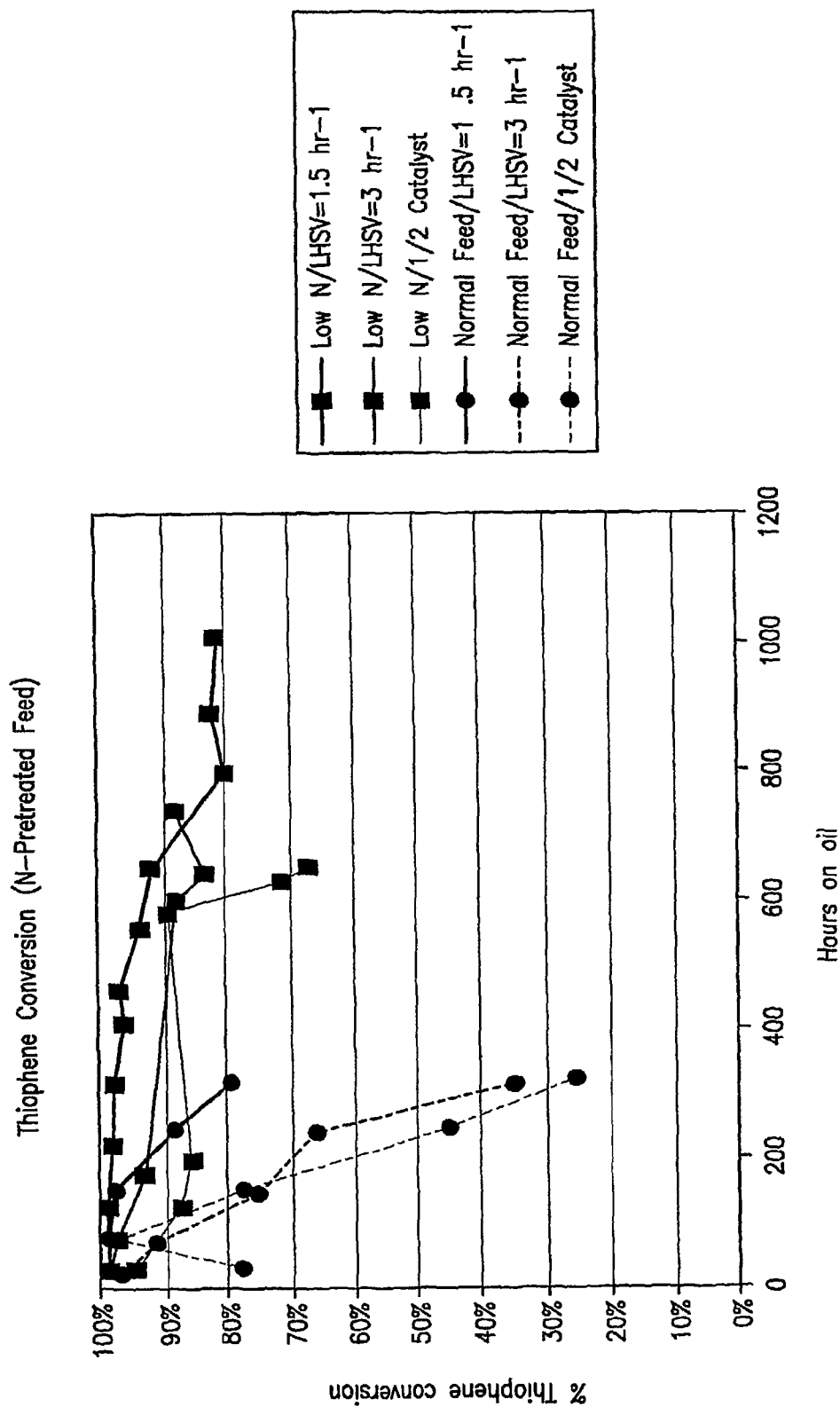

A series of experiments were conducted with the untreated commercial feed and the commercial feed that was acid washed and resin treated to remove the majority of the nitrogen in the feed. FIGS. 4, 5, and 6 below depict a plots that show thiophene conversion on the Y axis in molar percentage thiophene conversion units plotted as a function of total grams of feed, total grams of feed fed to the pilot plant reactor divided by the grams of catalyst loaded in the reactor and hours on oil, respectively for both the untreated feed and the acid washed-resin treated feeds at various different space velocities and catalyst loadings as indicated in figures. The pilot plant units were operated at (i) a space velocity of 1.5 hr$^{-1}$, (ii) a space velocity of 3.0 hr$^{-1}$ with the same catalyst quantity as loaded into (i) and doubling the feed flow rate, and (iii) a space velocity of 3.0 hr$^{-1}$ by reducing the catalyst quantity loaded into the reactor by ½ from the (i) case. The different space velocities were run to more clearly distinguish the effect of removing nitrogen from the feed. As can be seen from this data, the productivity of the catalyst (grams feed processed per gram of catalyst) at high thiophene conversion (>80%) is increased by greater than a factor of 3 when the feed was pretreated to remove the majority of nitrogen species is used. The majority of the nitrogen removed was non-basic nitrogen species for this commercial feedstock.

The pilot plant used in the present example is the same as the pilot plant described in Example 1.

The process conditions for each run where as follows except as set forth in FIGS. 4, 5, and 6.

| | |
|---|---|
| LHSV | as indicated in FIGS. 4, 5, and 6 |
| Temperature: | 180° C. |
| Pressure: | 400 psig |

An inspection of the plot clearly shows markedly reduced thiophene conversion activity in an acid catalyzed thiophene alkylation reaction for commercial feeds that contain non-basic nitrogen.

Example 4

Table 5 below shows the results of two titrations carried with two bases: pyridine and 2,6-di-tert-butyl pyridine on a commercially available solid phosphoric acid catalyst obtained from Süd-Chemie Inc. These titrations were carried out as follows:

The catalyst samples were crushed and sieved. Agglomerates with 180-355 mm diameters were loaded into a fixed bed pilot plant reactor. The samples (50 mg) were treated in flowing He (1.33 cm$^3$ s$^{-1}$) at 453 K for 1 h before taking titration measurements. Liquid mixtures of n-hexane (Fluka, 99.5%, 4.5 ml) with pyridine (Fischer, 99.9%, 20 ml) or 2,6-di-tert-butyl-pyridine (Aldrich, 97%, 50 ml) were prepared. The resulting mixture were introduced into a He stream (1.33 cm$^3$ s$^{-1}$) at a liquid volumetric flow rate of 0.09 cm$^3$ h$^{-1}$ resulting in mixtures with 0.3 kPa n-hexane and 5.3 Pa pyridine or 4.7 Pa 2,6-di-tert-butyl-pyridine. The temperature of the catalyst bed was 453° K. The amount of titrant adsorbed on the catalyst was calculated from its concentration in the effluent, measured by gas chromatography (Hewlett-Packard 6890 GC, 30 m HP-1 methyl silicone capillary column, flame ionization detector).

Without wishing to be bound by theory, Table 5 shows that there are two types of acid sites on the SPA catalysts: one set of strong acid sites (those titrated by the 2,6-di-tert-butyl pyridine) and one set of weaker acid sites (difference between those titrated by pyridine and those titrated by the 2,6-di-tert-butyl pyridine). It is believed that the strong acid sites are instrumental in effecting the thiophene conversion. These strong acid sites are selectively poisoned by non-basic nitrogen compounds since the non-basic compounds will not adsorb on the weak acid sites, but do react on the strong acid sites to yield products which are basic and then strongly adsorb on the strong acid sites. This reaction of the non-basic nitrogen compounds on the strong acid sites thereby removes the required sites for the thiophene alkylation accounts for the very high propensity for non-basic nitrogen compounds to poison the thiophene alkylation reaction.

TABLE 5

Titration of SPA

| Titrant | MW | Titrant µmole/g | Titrant g/g cat | G N/g cat g/g cat | Wt % N % |
|---|---|---|---|---|---|
| Pyridine | 78 | 612.5 | 0.047775 | 0.008575 | 0.86% |
| 2,6-di-tert-butyl pyridine | 192 | 214.4 | 0.041165 | 0.003002 | 0.30% |

Therefore, from the above examples, it is apparent that there is a significant need for a process to effectively remove a wide variety of nitrogen compounds, especially the non-basic nitrogen compounds, from the commercial thiophene alkylation feed. The following examples disclose process options in accordance with the present invention that are suitable for removing these non-basic nitrogen compounds from a commercial thiophene alkylation feedstock.

Example 5

The experiments described in this example have been carried out in a multiple fixed bed adsorption system. Four fixed bed stainless steel reactors were connected in parallel to a common feed inlet. Liquid feed was introduced by means of a double piston pump, able to maintain a constant flow minimizing the piston pulses. The system design permitted upflow or down-flow of the feed through an adsorbent bed. Cumulative liquid samples were taken at the outlet of the tubes at predetermined time intervals and analysed by gas chromatography.

A Varian-3380 GC equipped with an FID and a Pulsed Flame Photometric Detector (PFPD) working in the nitrogen mode was used for analysing the outlet stream. Propionitrile, butyronitrile, pyrrole and thiophene are detected by the PFPD, whereas heptane and hexene-1 are detected by the FID, with both detectors working in parallel. The different compounds were separated in a CP-Sil 24-CB column.

The adsorption experiments were carried out at room temperature, at a pressure of 3.5 bar, and WHSV in the range of 15-20 h$^{-1}$. The amount of adsorbent used was 2 grams, and in all cases it had been dried (2 h/200° C. in 100 ml N$_2$ flow) and compacted with n-heptane before introducing the nitrogen-containing feed at a constant flow of around 1.0 ml/min. The space velocity was determined in each case on the basis of the amount of processed feed recovered at the outlet of the reactors.

Butyronitrile Adsorption

Sepiolite

The adsorbents used and their main characteristics are described in Table 6. In the run using a commercial solid phosphoric acid catalyst, the original catalyst pellets were crushed and sieved to a particle size of 0.4-0.6 mm, and the adsorption has been performed twice in order to check the reproducibility of the experimental protocol. The remaining adsorbents were similarly pressed, crushed and sieved to the same particle range (0.4-0.6 mm) except for the FCC ECAT, which was already in microsphere form.

The base model feed contained n-heptane (50 wt %), hexene-1 (50 wt %) and thiophene (200 ppmw S), and was spiked with 80 ppmw nitrogen as Butyronitrile. This model feed was passed through the adsorbents described above in Table 6.

Adsorption Results

Figure 7:
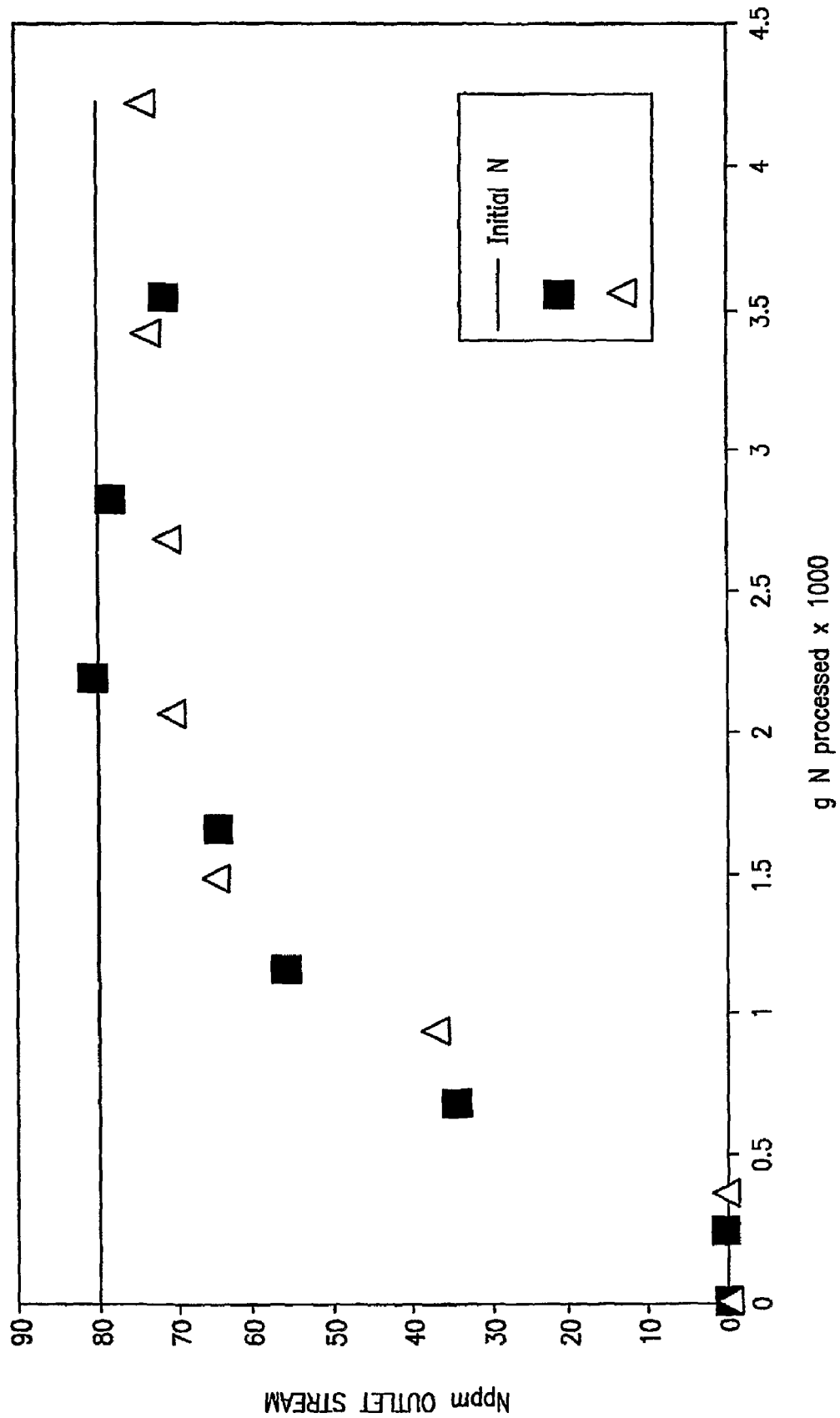
FIGS. 7 through 11 show butyronitrile adsorption capacity for various adsorbents.

Results for the commercial solid phosphoric acid catalyst are depicted in FIG. 7 (breakthrough curve) and Table 7, and show there is a good reproducibility. The values set forth in Table 7 as adsorption capacities are determined as the amount of N adsorbed per 100 g adsorbent, just before any N is detected in the effluent stream. It can be seen that the adsorption capacity for butyronitrile in these conditions is relatively low.

Figure 8:
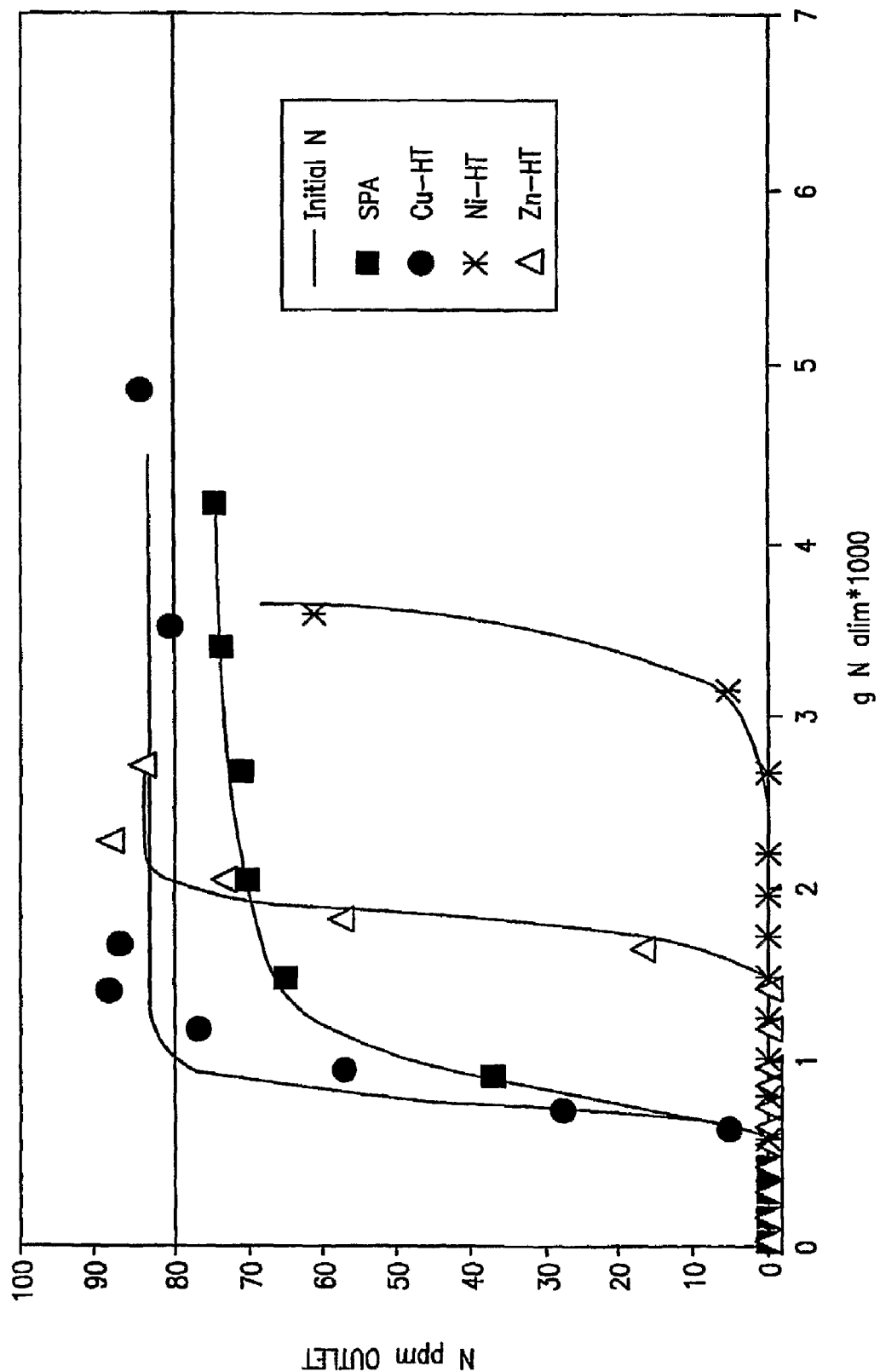
Figure 9:
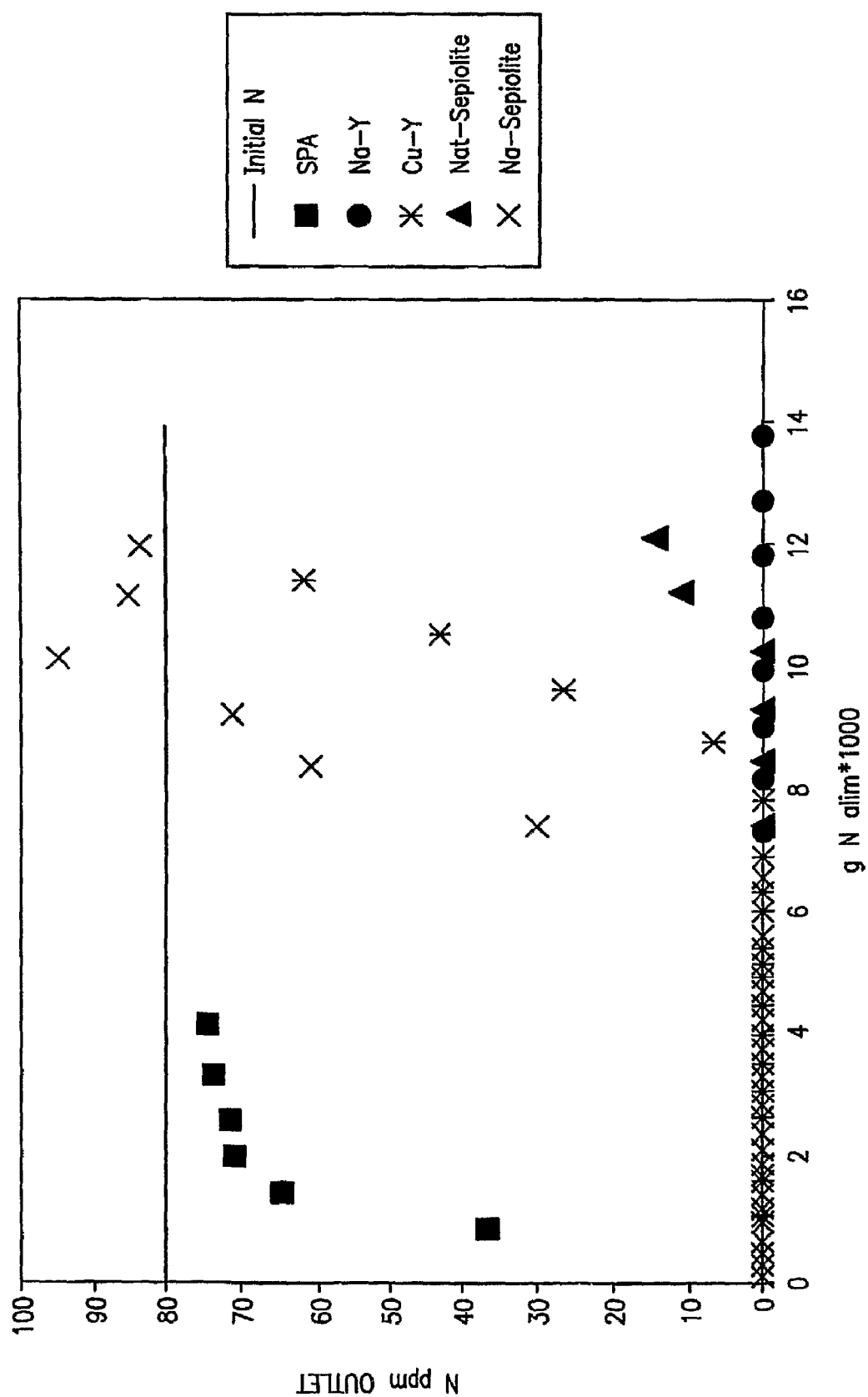
Figure 10:
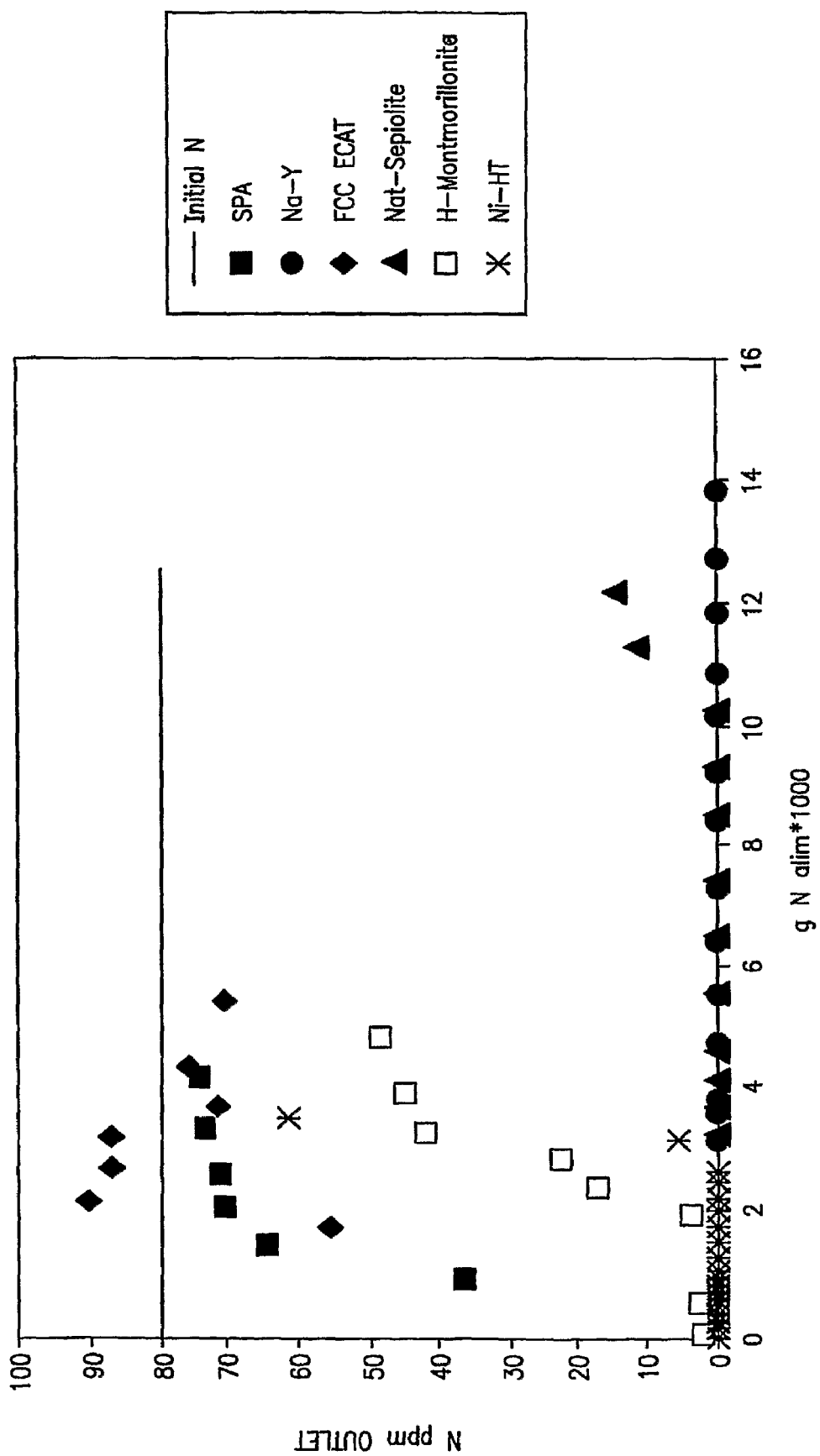
Figure 11:
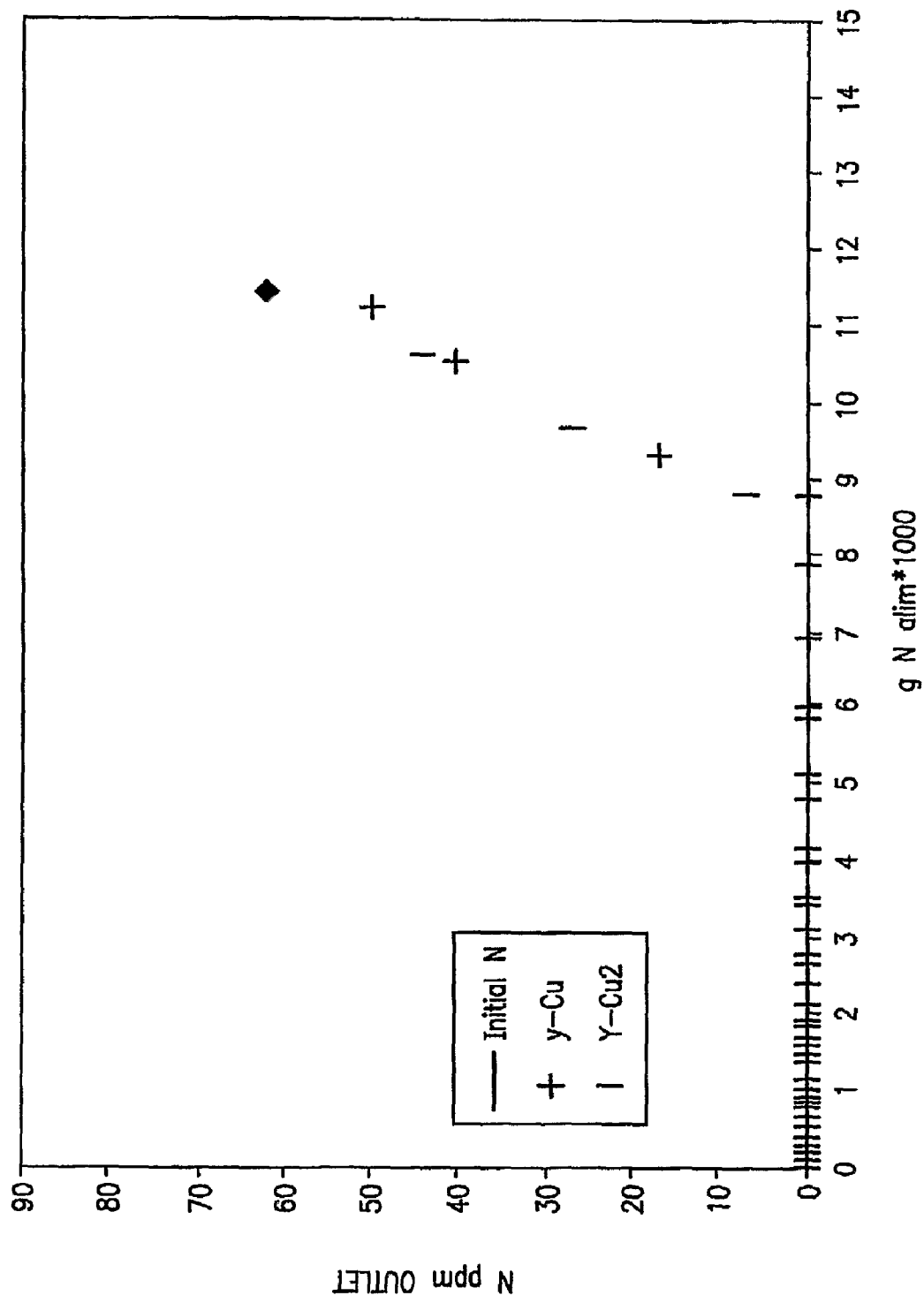

The comparative results for the remaining adsorbents are also set out in Table 7 and depicted in FIGS. 9 through 11. In FIG. 8, commercial solid phosphoric acid catalyst is compared with different hydrotalcite based adsorbents. FIG. 9 shows a comparison of commercial solid phosphoric acid with two Y zeolites, a commercial Na—Y (CBV-100, obtained from Zeolyst Intl.), Cu-exchanged Y, two sepiolites: a natural sepiolite and a Na-exchanged sepiolite. FIG. 10 compares the commercial solid phosphoric acid with an FCC ECAT, an acid exchanged montmorillonite, and with the adsorbents based on hydrotalcites, Y zeolite and sepiolite. After passing 173 g of feedstock through the 2 g bed of NaX adsorbent in the conditions described above, no butyronitrile was detected in the outlet stream. Thus, the copper exchanged Na—Y had a minimum nitrogen adsorption capacity of 0.69 g N/100 g adsorbent.

The copper exchanged Y zeolite also showed a considerable adsorption capacity. This test was repeated and the data was confirmed as can be seen in Table 7 and FIG. 11. Finally the sepiolite based adsorbents give also high butyronitrile adsorption capacities.

TABLE 6

Adsorbents Used for Removal of Butyronitrile

| Adsorbent | Characteristics |
|---|---|
| Na-Y zeolite | CBV-100 (Zeolyst Intl.), Si/Al = 2.6 |
| Natural magnesium silicate | Natural fibrous magnesium silicates with crystalline structure |
| Commercial solid phosphoric acid | Solid phosphoric acid catalyst supplied by Sud Chemie |
| Equilibrium Fluidized Cracking Catalyst | FCC ECAT, 800 ppm Ni, 2000 ppm V, UCS = 24.32 Å |
| H-Montmorillonite | Acid treated montmorillonite (6 h, 0.2 M HCl solution, room T) |
| Cu-Hydrotalcite | Al$^{3+}$/(Al$^{3+}$ + Cu$^{2+}$ + Mg$^{2+}$) = 0.25; Cu2+/(Cu$^{2+}$ + Mg$^{2+}$) = 0.5 (molar ratios) |
| Zn-Hydrotalcite | Al3+/(Al3+ + Zn2+ + Mg2+) = 0.25; Zn2+/(Zn2+ + Mg2+) = 0.5 (molar ratios) |
| Ni-Hydrotalcite | Al3+/(Al3+ + Ni2+ + Mg2+) = 0.25; Ni2+/(Ni2+ + Mg2+) = 0.13 (molar ratios) |
| Cu—Na Y zeolite | Cu exchanged CBV-100 (2.7 wt % Na2O, 15.8 wt % CuO) |
| Na-exchanged | Na exchanged natural sepiolite (4.4 wt % Na2O) |

TABLE 7

Adsorption Capacities for the Different Adsorbents

| Adsorbent | WHSV (h-1) | Pressure (bar) | Adsorption capacity (gN/100 g adsorbent) |
|---|---|---|---|
| BP catalyst | 16.7 | 3.25 | 0.012 |
| BP catalyst | 19.3 | 3.25 | 0.018 |
| FCC ECAT | 18.2 | 3.5 | 0.063 |
| H-Montmorillonite | 16.8 | 3.5 | 0.074 |
| Cu-Hydrotalcite | 16.5 | 3.5 | 0.027 |
| Zn-Hydrotalcite | 17.7 | 3.5 | 0.071 |
| Ni-Hydrotalcite | 16.4 | 3.5 | 0.13 |
| Cu—Y zeolite | 15.8 | 3.5 | 0.44 |
| Cu—Y zeolite | 16.9 | 3.5 | 0.40 |
| Na—Y zeolite | 16.1 | 3.5 | 0.69 |
| Natural Sepiolite | 17.3 | 3.5 | 0.51 |
| Na-Sepiolite | 17.4 | 3.5 | 0.33 |

Example 6

Propionitrile and Pyrrole Adsorption

Figure 12:
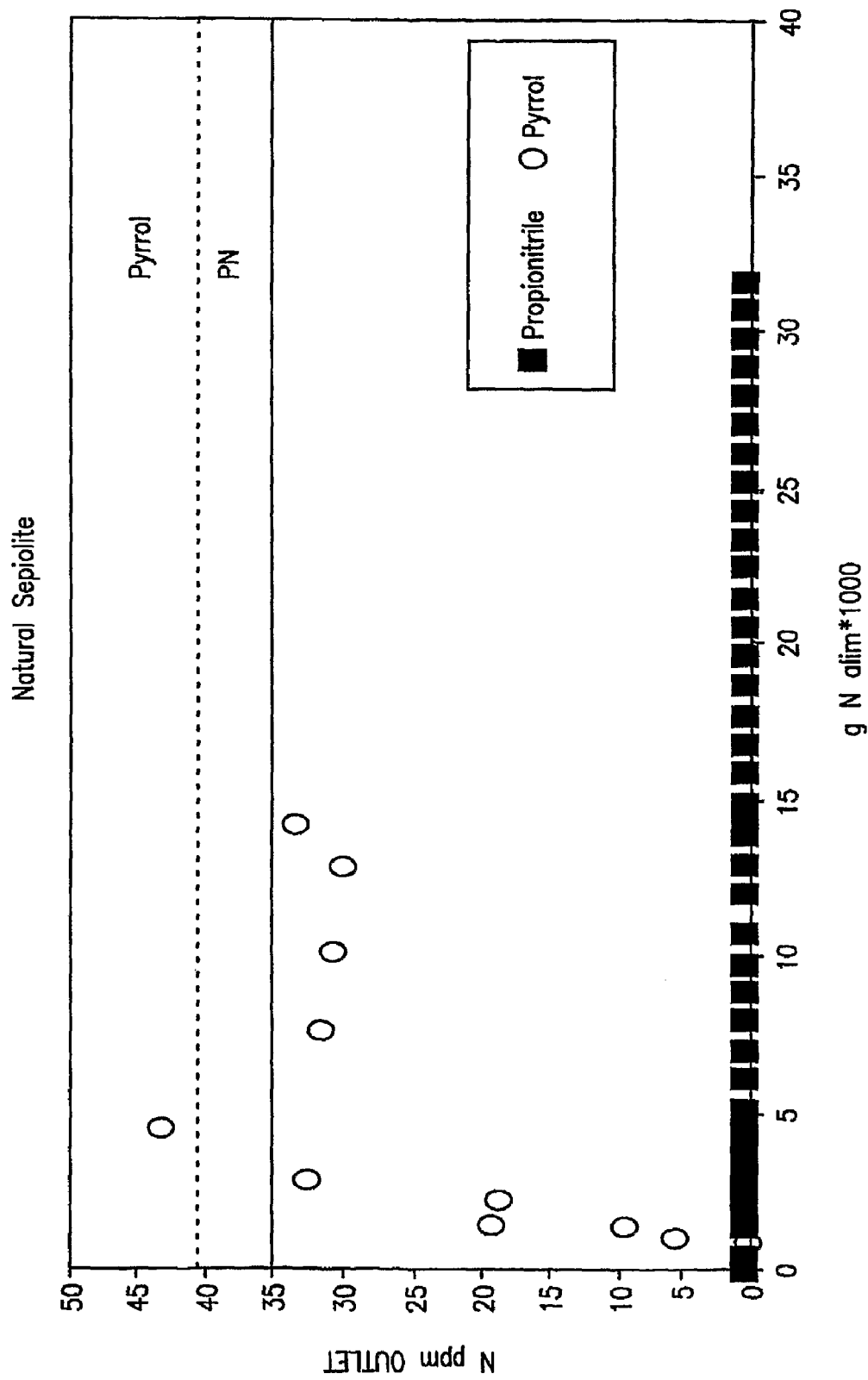
FIGS. 12 and 13 show breakthrough curves for adsorption of pyrrole and propionitrile.
Figure 13:
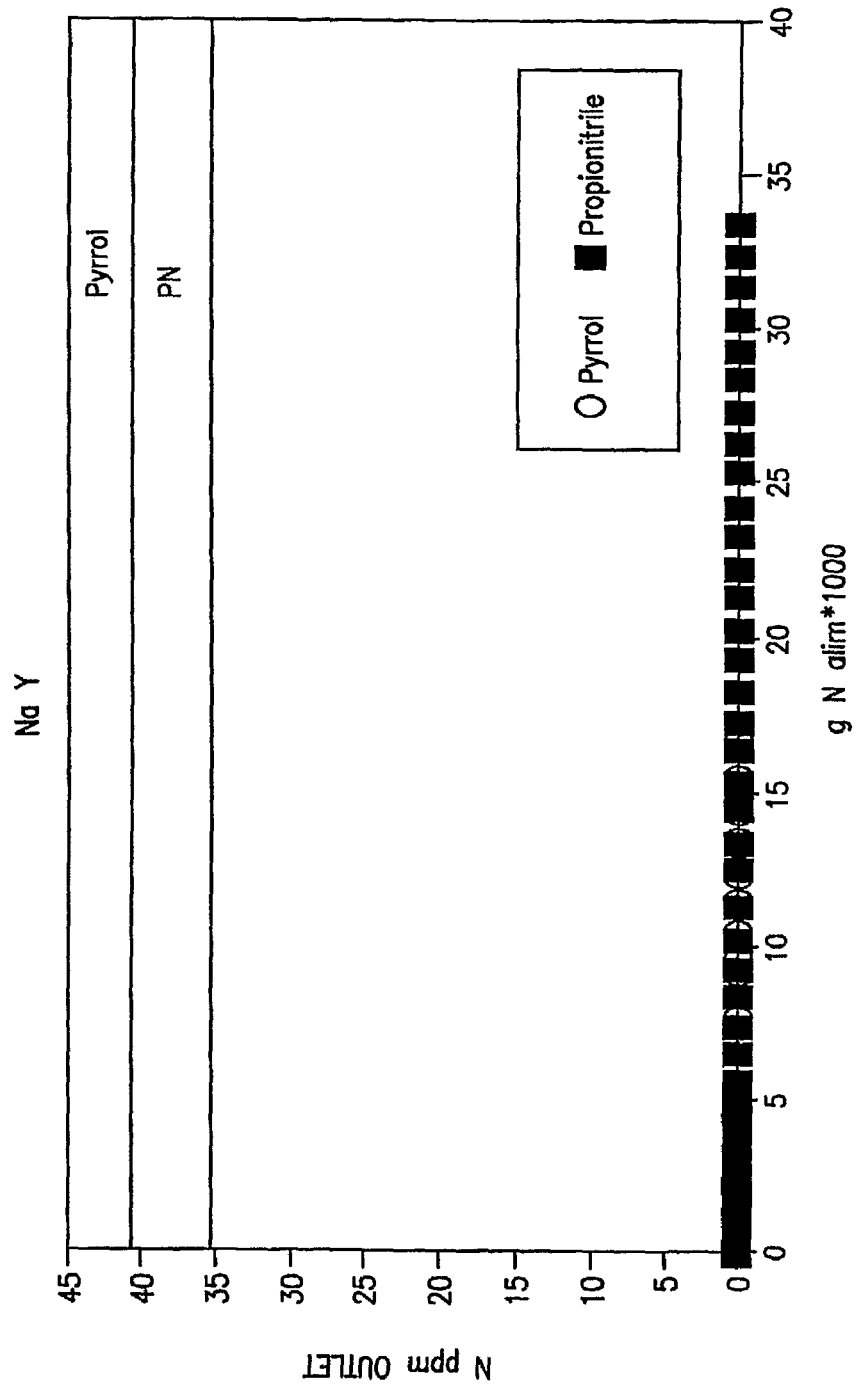

In this example the base model feed contained n-heptane (50 wt %), hexene-1 (50 wt %) and thiophene (200 ppmw S) and was spiked with 40 ppm of propionitrile and 40 ppm of pyrrole. This feed was passed through Na—Y and Sepiolite adsorbents in order to evaluate the relative adsorption capacities of each adsorbent with respect to each nitrogen compound. Breakthrough curves of adsorption are shown in FIGS. 12 and 13. Nitrogen adsorption capacities are summarized in Table 8.

TABLE 8

Nitrogen compounds adsorption capacity of Na—Y and Sepiolite adsorbents. WHSV 15-20 hr$^{-1}$, room temperature, 4 bar (spiked with 40 ppmN of each N-compound) gr N/100 gradsorbent

| | | Gr N/100 gr adsorbent | | |
|---|---|---|---|---|
| | Adsorbent | Pyrrole | PN | Sum |
| Base Feed | NA—Y | >0.52 | >0.83 | >1.35 |
| | Sepiolite | 0.05 | >0.76 | >0.84 |

TABLE 8-continued

Nitrogen compounds adsorption capacity of Na—Y and Sepiolite adsorbents. WHSV 15-20 hr$^{-1}$, room temperature, 4 bar (spiked with 40 ppmN of each N-compound) gr N/100 gradsorbent

| | | Gr N/100 gr adsorbent | | |
|---|---|---|---|---|
| | Adsorbent | Pyrrole | PN | Sum |
| Base Feed + | NA—Y | 0.1 | >1.3 | >1.4 |
| 30% Aromatics | Sepiolite | 0.017 | 0.28 | 0.3 |

Example 7

Effect of Aromatics on Propionitrile and Pyrrole Adsorption

Figure 14:
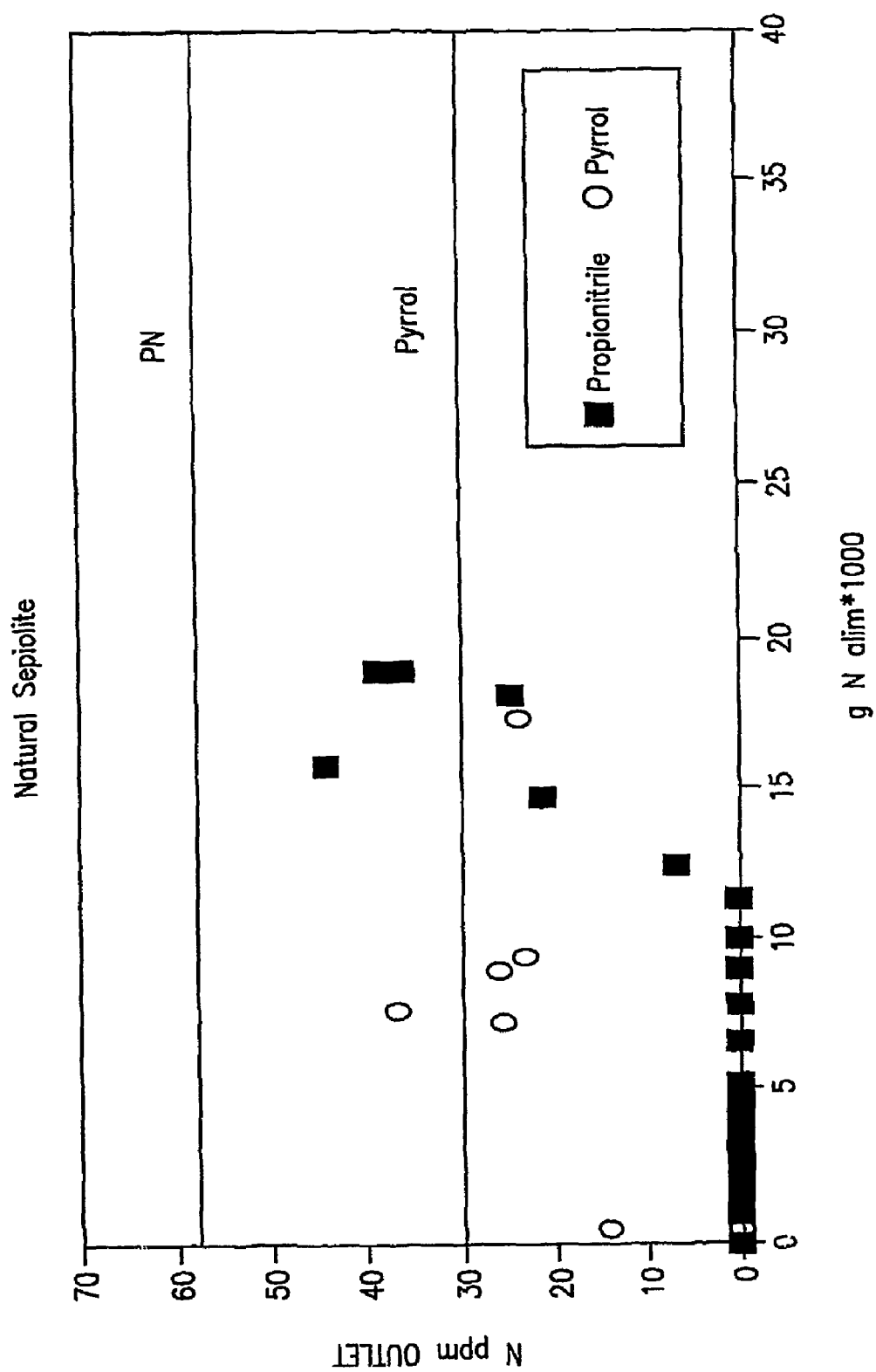
FIGS. 14 and 15 show breakthrough curves for adsorption of propionitrile and pyrrole in the presence of a feedstock containing aromatics.
Figure 15:
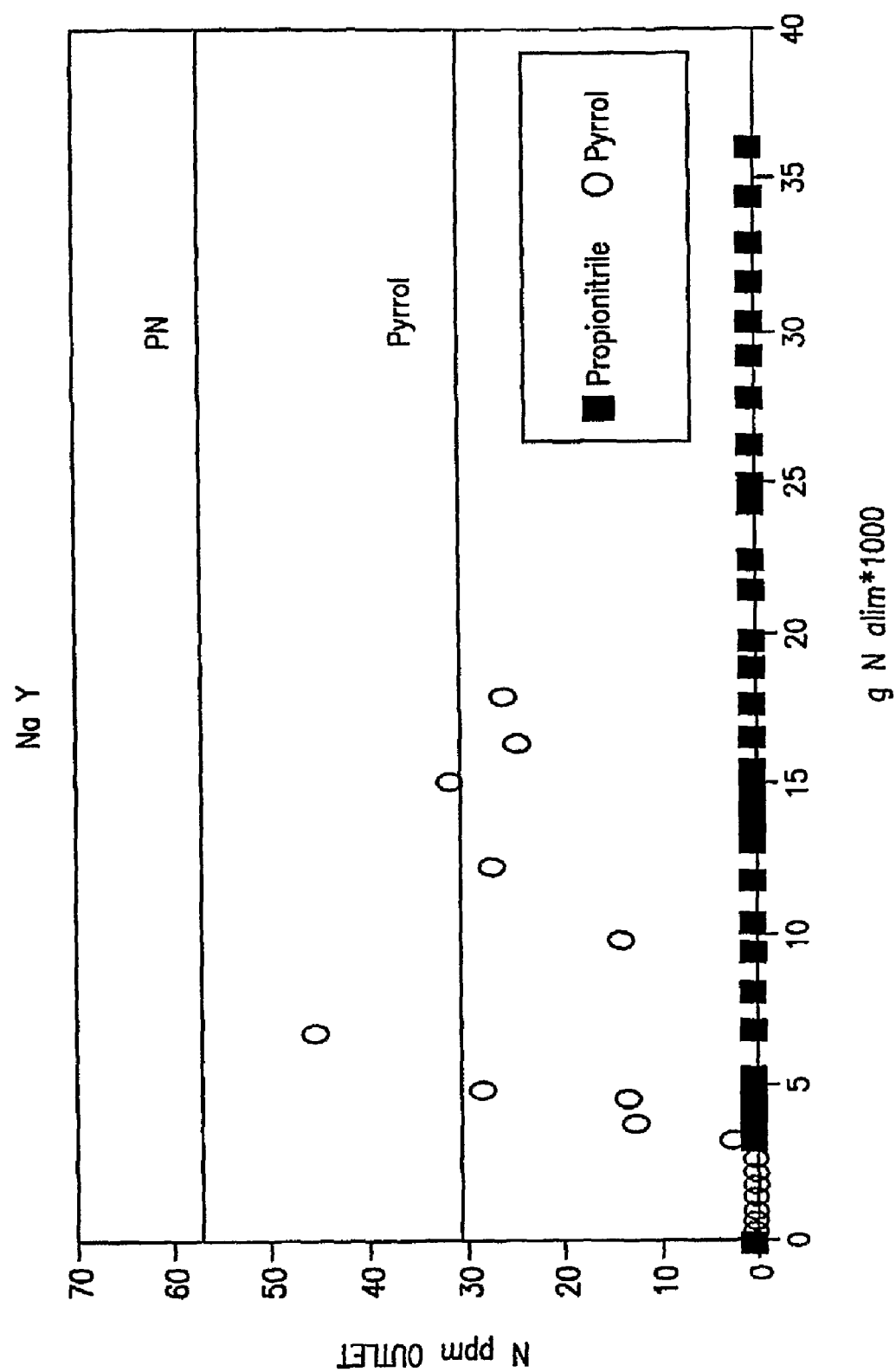

In order to evaluate the influence of the presence of aromatics in the feed, the following model feed was prepared: 35% n-heptane, 35% 1-Hexene, 22% Toluene, 8% o-Xylene, 200 ppm Thiophene and 40 ppm PN and 40 ppm Pyrrole. This feed was passed through Na—Y and Sepiolite adsorbents. Breakthrough curves of adsorption of these experiments are shown in FIGS. 14 and 15. These breakthrough curves were obtained at 15-20 hr$^{-1}$ WHSV, room temperature, and a pressure of 4 Bar. The effect of aromatics in the nitrogen capacity can be also observed in Table 8, where the adsorption capacities are shown.

Example 8

NaY Regeneration

The adsorption on fresh NaY shows a high adsorption capacity for propionitrile and pyrrole when a base feed spiked with 80 ppm N as propionitrile and 80 ppm N as pyrrole is passed through zeolite placed in a fixed bed.

The regeneration of used NaY was carried out either by calcination at 200° C. for 12 hours or by washing.

Regeneration by washing was carried out with toluene at a temperature of about 20° C., a flow of 5 mil/min, at atmospheric pressure for about 20 hours.

The regeneration by washing appeared to provide improved results over the regeneration by calcinations; 10% more propionitrile and pyrrole was adsorbed on the washed catalyst.

TABLE 9

| WHSV (h$^{-1}$) | Catalyst | Pressure (bar) | Feed | Propionitrile (gN ads/100 g Catalyst) | Pyrrole (gN ads/ 100 g Catalyst) | Butyronitrile (gN ads/ 100 g Catalyst) |
|---|---|---|---|---|---|---|
| 13.84 | NaY | 4 | BF + 80 ppm N PN 80 ppm N Py | >2.06 | 1.48 | — |
| 25.86 | NaY1 | 4 | BF + 160 ppm N PN 160 ppm N Py | >1.2 | 0.99 | — |
| 19.86 | NaY2 | 4 | BF + 160 ppm N PN 160 ppm N Py | >1.35 | 1.12 | — |

1. - NaY regeneration by calcinations (200° C.)
2. - NaY regeneration by washed with Toluene at room temperature
BF - 50% nC7 and 50%
1C6 = spiked with 200 ppm S as Thiophene

Example 9

Competitive Adsorption

When 40 ppm N as Butyronitrile was added to the feed in Example 7, it can be observed that the pyrrole adsorption capacity decreased. There was a decrease in propionitrile adsorption capacity as well. It is believed this was produced by the competition between PN and BN for the zeolite active sites; however, it seems that adsorption of the two nitriles prevents adsorption of pyrrole occupying the active centers. This becomes evident when we compare Table 9 with Table 10. The Table 10 shows two identical and simultaneous adsorptions.

TABLE 10

| WHSV (h⁻¹) | Catalyst | Feed | Propionitrile (gN ads/ 100 g Catalyst) | Butyronitrile (gN ads/ 100 g Catalyst) | Pyrrole (gN ads/ 100 g Catalyst) |
|---|---|---|---|---|---|
| 70.52 | NaY | BF + 80 ppm N PN 80 ppm N Py 40 ppm N BN | 0.8851 | 0.728 | 0.2651 |
| 80.88 | NaY | BF + 80 ppm N PN 80 ppm N Py 40 ppm N BN | 1.0023 | 0.7439 | 0.2733 |

Table 11 shows a summary of the adsorption capacity of sepiolites and zeolite Y in Na—, Na—H, H—, Cu—, and Cs— form, when using base feed containing pyrrol, propionitrile, and butyronitrile (determined from above to be the 3 most significant poisoning compounds in the typical commercial feed).

Table 11 shows the amounts of N adsorbed when the first compound breaks through.

TABLE 11

| Catalyst | Propionitrile (gN ads/100 g Catalyst) | Pyrrole (gN ads/100 g Catalyst) | Butyronitrile (gN ads/100 g Catalyst) | Sum | "N" free feed |
|---|---|---|---|---|---|
| Natural sepiolite | 0.0486 | 0.049 | — | 0.0976 | 24.29 |
| Natural sepiolite BF + 30% aromatics | 0.02256 | 0.017 | — | 0.03956 | 11.28 |
| NaY | >0.8353 | >0.5152 | — | >1.3505 | 417.67 |
| NaY BF + 30% aromatics | 0.1965 | 0.1 | — | 0.2965 | 68.14 |
| HY | 0.145 | 0.4646 | 0.0153 | 0.6249 | 48.69 |
| NaHY | 0.209 | 0.6678 | 0.0221 | 0.8989 | 69.99 |
| CuNaY | 0.0961 | 0.3072 | 0.0101 | 0.4134 | 32.2 |
| NaX | 0.241 | 0.7701 | 0.0254 | 1.0365 | 80.71 |
| CsY | 0.3198 | 1.5908 | 0.086 | 1.9953 | 70.02 |

Shadowed Cells = first breaking compound

Table 12 shows the values for N that the solids were able to absorb.

TABLE 12

| Catalyst | Propionitrile (gN ads/ 100 g Catalyst) | Pyrrole (gN ads/100 g Catalyst) | Butyronitrile (gN ads/ 100 g Catalyst) | Sum | WHSV |
|---|---|---|---|---|---|
| Natural sepiolite | >0.79 | 0.049 | — | 0.839 | 17.88 |
| Natural sepiolite BF + 30% aromatics | 0.283 | 0.017 | — | 0.3 | 19.65 |
| NaY | >0.8353 | >0.5152 | — | >1.3505 | 18.84 |
| NaY BF + 30% aromatics | >1.3 | 0.1 | — | >1.4 | 20.21 |
| HY | 0.145 | 0.818 | 0.0199 | 0.9829 | 80.59 |
| NaHY | 0.3 | 0.67 | 0.0283 | 0.9938 | 69.37 |
| CuNaY | 0.3203 | 0.3072 | 0.0161 | 0.64 | 67.75 |
| NaX | >0.7 | 0.77 | 0.0584 | 1.5248 | 67.86 |
| CsY | 0.3198 | 1.5908 | 0.0846 | 1.9952 | |

From Table 12, it is evident that zeolite NaY and CuY are effective adsorbents for non-basic nitrogen compounds. It should be noticed that aromatics compete for adsorption sites, and this is more important for pyrrole. CsY zeolite adsorbed less propionitrile than NaY, but more pyrrole, while the adsorption of butyronitrile was also high. Taking this into account and from Tables 12 and 13 above, a mixture of adsorbents could be an effective non-basic nitrogen compound pretreatment for the thiophene alkylation process. As mentioned above, regeneration can be achieved and adsorption capacity restored by heating in a flow of air, or by washing with toluene.

Example 10

In this example, the effect of feed pre-treatment to remove non-basic nitrogen compounds with a commercial thiophene alkylation feed was demonstrated (See Table 4). Commercial thiophenen alkylation feed was passed in parallel through two fixed beds, one containing Na—Y, and the second containing Sepiolite. Nitrogen absorption conditions were 70° F., WHSV=15 hr⁻¹, with 2 grams of adsorbent material. The product from the adsorbent reactor was collected every 80 minutes. The following feeds were collected for evaluation in a thiophene alkylation reactor.

| Commerical Feed | No Pretreatment | |
|---|---|---|
| Feed NaY-1 | Na—Y Adsorbent | 0-180 minutes (80 grams) |
| Feed NaY-2 | Na—Y Adsorbent | 180-340 minutes (80 grams) |
| Feed NaY-3 | Na—Y Adsorbent | 340-510 minutes (80 grams) |

-continued

| Commerical Feed | No Pretreatment | |
|---|---|---|
| Feed NaY-4 | Na—Y Adsorbent | 510-730 minutes (108 grams) |
| Feed Sep-1 | Sepiolite Adsorbent | 0-180 minutes (80 grams) |
| Feed Sep-2 | Sepiolite Adsorbent | 510-730 minutes (108 grams) |

The solid phosphoric acid catalyst used in the pilot plant runs of the present example was the commercially available catalyst designated as C-84-05 obtained from Sud Chemie Inc. The pilot plant was loaded with 300 mg of a solid phosphoric acid catalyst which was crushed to a Tyler screen mesh size of 0.4-0.6 mm. The catalyst was dried under nitrogen flow for 2 hours at 200° C. prior to use. The pilot plant consisted of parallel fixed bed reactors, each capable of holding between 50 to 1000 mg of catalyst. The pilot plant design is similar to that described in example 1 above. The reactors were operated in a downflow operation. Each of the above feeds were run in this pilot plant sequence.

The conditions used for each run included:

| | | |
|---|---|---|
| | LHSV | 4.1 hr$^{-1}$ |
| | Pressure | 400 psig |
| | Temperature | 180° C. |

Figure 16:
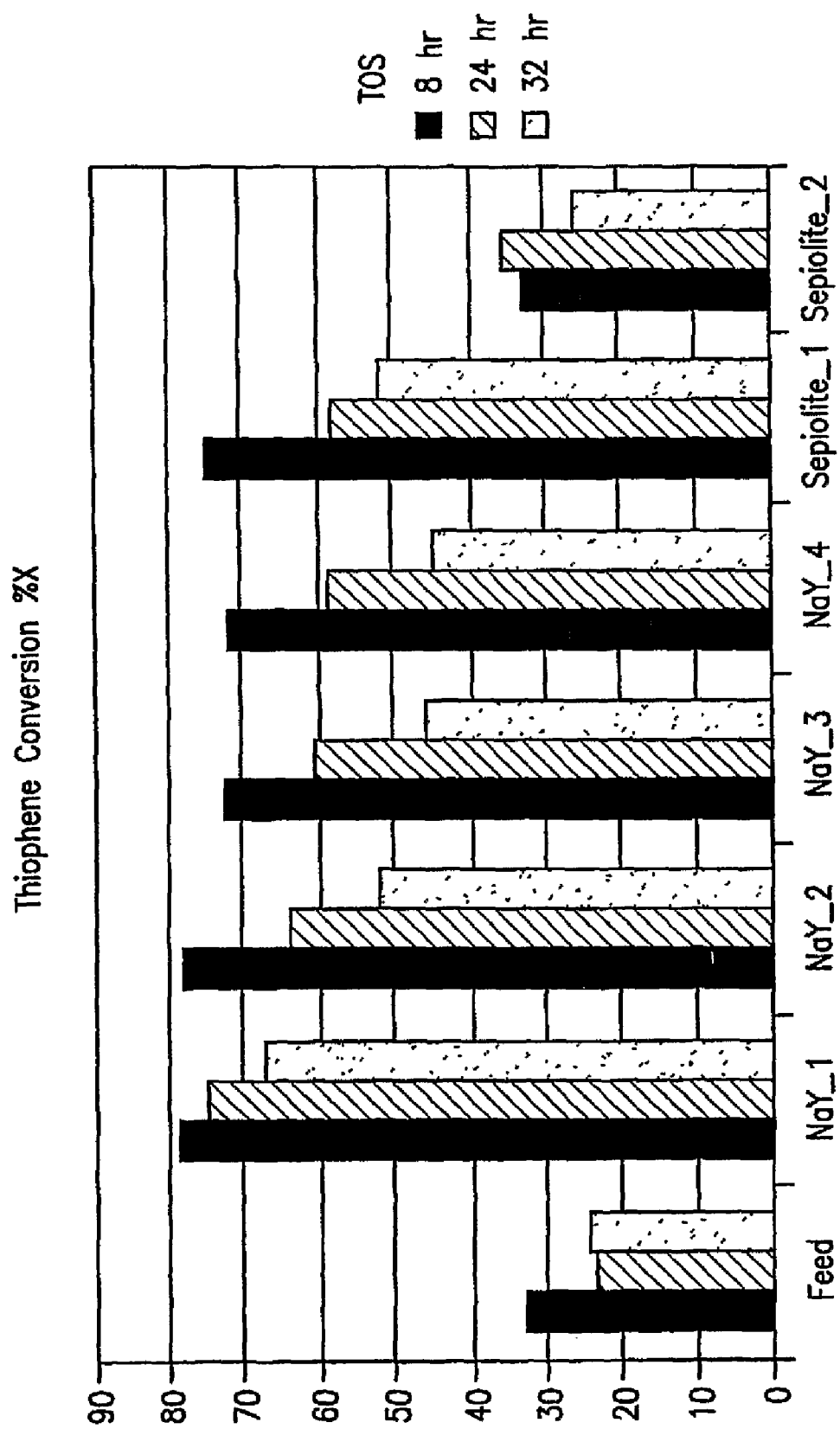
FIG. 16 shows the thiophene conversion results of various feeds treated for different periods with different adsorbents.

The results of this set of experiments is shown in FIG. 16. It is evident from the results the strong improvement in catalyst performance achieved for the thiophene alkylation process when the commercial feed was pretreated with either NaY or Sepiolite. This compares with the rapid deactivation seen with the untreated commercial feed after only 8 hours on stream. Stable performance is seen from the NaY pre-treatment over the range evaluated (up to 150 grams of feed treated per gram of Adsorbent).

That which is claimed is:

1. A process for the production of products which are liquid at ambient conditions and contain organic sulfur compounds of higher molecular weight than corresponding sulfur-containing compounds in the feedstock, which process comprises:
   providing a hydrocarbon feedstock comprising material boiling between about 60° C. and about 425° C. comprising sulfur-containing compounds at a level of sulfur up to about 5,000 parts per million and nitrogen-containing compounds at a level of nitrogen up to about 2000 parts per million, including non-basic nitrogen-containing compounds at a level up to about 200 parts per million, and a high content of olefins of up to about 60 weight percent;
   removing the non-basic nitrogen containing compounds from the aforesaid feedstock by an adsorption process to yield an effluent having a reduced amount of aforesaid non-basic nitrogen-containing compounds, wherein the adsorbent used in the adsorption process is selected from the group consisting of alkaline faujisite-type zeolites, alkaline earth faujisite-type zeolites, alkaline faujisite-type zeolites partially exchanged with H$^+$ or transition metals of Groups IB, IIB, IV, VIII, and mixtures thereof, alkaline earth faujisite-type zeolites partially exchanged with H$^+$ or transition metals of Groups IB, IIB, IV, VIII, and mixtures thereof, crystalline magnesium silicates, and alkaline exchanged crystalline magnesium silicates, and mixtures thereof; and
   contacting the aforesaid effluent with an acidic catalyst under alkylation conditions which are effective to convert a portion of the sulfur-containing compounds to higher molecular weight and higher boiling sulfur-containing compounds through alkylation by the aforesaid olefins and to produce a liquid effluent containing such higher molecular weight and higher boiling sulfur-containing compounds.

2. The process of claim 1 wherein the adsorbent is regenerated with an organic solvent.

3. The process of claim 2 wherein the organic solvent contains one aromatic ring.

4. The process of claim 3 wherein the solvent is selected from the group consisting of benzene and alkylbenzenes having a total number of carbon atoms of eleven or less.

5. The process of claim 2 wherein the solvent is an aliphatic alcohol having twelve or less carbon atoms.

6. The process of claim 1 wherein the adsorbent is a sepiolite in the natural form or in the alkaline exchanged form.

7. A process for the production of products which are liquid at ambient conditions and contain organic sulfur compounds of higher molecular weight than corresponding sulfur-containing compounds in the feedstock, which process consists essentially of:
   providing a hydrocarbon feedstock comprising material boiling between about 60° C. and about 425° C. comprising sulfur-containing compounds at a level of sulfur up to about 5,000 parts per million and nitrogen-containing compounds at a level of nitrogen up to about 2000 parts per million, including non-basic nitrogen-containing compounds at a level up to about 200 parts per million, and a high content of olefins of up to about 60 weight percent;
   removing the non-basic nitrogen containing compounds from the aforesaid feedstock by an adsorption process to yield an effluent having a reduced amount of aforesaid non-basic nitrogen-containing compounds wherein the adsorbent used in the adsorption process is selected from the group consisting of alkaline faujisite-type zeolites, alkaline earth faujisite-type zeolite, alkaline faujisite-type zeolites partially exchanged with H$^+$ or transition metals of Groups IB, IIB, IV, VIII, and mixtures thereof, alkaline earth faujisite-type zeolites partially exchanged with H$^+$ or transition metals of Groups IB, IIB, IV, VIII, and mixtures thereof, crystalline magnesium silicates, and alkaline exchanged crystalline magnesium silicates, and mixtures thereof; and
   contacting the aforesaid effluent with an acidic catalyst under alkylation conditions which are effective to convert a portion of the sulfur-containing compounds to higher molecular weight and higher boiling sulfur-containing compounds through alkylation by the aforesaid olefins and to produce a liquid effluent containing such higher molecular weight and higher boiling sulfur-containing compounds.

* * * * *